(12) United States Patent
Pecker et al.

(10) Patent No.: US 7,101,706 B1
(45) Date of Patent: Sep. 5, 2006

(54) POLYNUCLEOTIDES AND POLYPEPTIDES ENCODED THEREBY DISTANTLY HOMOLOGOUS TO HEPARANASE

(75) Inventors: Iris Pecker, Rishon le Zion (IL); Israel Michal, Ashkelon (IL); Hanan Itzhaki, Nes Ziona (IL)

(73) Assignee: InSight Biopharmaceuticals Ltd., Rehovot (IL)

( * ) Notice: Subject to any disclaimer, the term of this patent is extended or adjusted under 35 U.S.C. 154(b) by 712 days.

(21) Appl. No.: 09/959,643

(22) PCT Filed: Jun. 19, 2000

(86) PCT No.: PCT/IL00/00358

§ 371 (c)(1),
(2), (4) Date: Nov. 2, 2001

(87) PCT Pub. No.: WO01/00643

PCT Pub. Date: Jan. 4, 2001

Related U.S. Application Data

(60) Provisional application No. 60/140,801, filed on Jun. 25, 1999.

(51) Int. Cl.
  *C12N 5/00*      (2006.01)
  *C12N 15/63*     (2006.01)
  *C70H 21/02*     (2006.01)
  *C07H 21/04*     (2006.01)

(52) U.S. Cl. ............ 435/325; 435/455; 536/23.1; 536/23.2

(58) Field of Classification Search .......... 536/23.2, 536/23.1; 435/455, 458, 6, 91.1, 325
See application file for complete search history.

(56) References Cited

U.S. PATENT DOCUMENTS 5,332,671 A * 7/1994 Ferrara et al. ............ 435/360

OTHER PUBLICATIONS

Marra, M. et al. The WashU–HHMI Mouse EST Project, Accession No. AI019269.*
Vlodavsky et al, (1999). Mammalian heparanase: gene cloning, expression and function in tumor progression and matastasis. Nature Medicine, vol. 5, No. 7, Jul. 1999, pp. 793–802.

* cited by examiner

*Primary Examiner*—John L. LeGuyader
*Assistant Examiner*—Jane Zara
(74) *Attorney, Agent, or Firm*—G. E. Ehrlich (1995) Ltd.

(57) ABSTRACT

The present invention relates to novel polynucleotides encoding polypeptides homologous to heparanase, nucleic acid constructs including these novel polynucleotides, genetically modified cells expressing the same, recombinant proteins encoded thereby and which may have heparanase or other glycosyl hydrolase activity, antibodies recognizing the recombinant proteins, oligonucleotides, analogs thereof and ribozymes derived from these polynucleotides.

3 Claims, 8 Drawing Sheets

```
                                CGCTTAATTCTAGAAGAGGGATTGA     25
ATGAGGGTGCTTTGTGCCTTCCCTGAAGCCATGCCCTCCAGCAACTCCCGCCCCCCGCG   85
 M  R  V  L  C  A  F  P  E  A  M  P  S  S  N  S  R  P  P  A

TGCCTAGCCCCGGGGGCTCTCTACTTGGCTCTGTTGCTCCATCTCTCCCTTTCCTCCAG  145
 C  L  A  P  G  A  L  Y  L  A  L  L  L  H  L  S  L  S  S  Q

GCTGGAGACAGGAGACCCTTGCCTGTAGACAGAGCTGCAGGTTTGAAGGAAAAAGACCCTG 205
 A  G  D  R  R  P  L  P  V  D  R  A  A  G  L  K  E  K  T  L

ATTCTACTTGATGTGAGCACCAAGAACCCAGTCAGGACAGTCAATGAGAACTTCCTCTCT  265
 I  L  L  D  V  S  T  K  N  P  V  R  T  V  N  E  N  F  L  S

CTGCAGCTGGATCCGTCCATCATTCATGATGGCTGGCTCGATTTCCTAAGCTCCAAGCGC  325
 L  Q  L  D  P  S  I  I  H  D  G  W  L  D  F  L  S  S  K  R

TTGGTGACCCTGGCCCGGGGACTTTCGCCCGCCTTTCTGCGCTTCGGGGGCAAAAGGACC  385
 L  V  T  L  A  R  G  L  S  P  A  F  L  R  F  G  G  K  R  T

GACTTCCTGCAGTTCCAGAACCTGAGGAACCCGGCGAAAAGCCGCGGGGGCCCGGGCCCG  445
 D  F  L  Q  F  Q  N  L  R  N  P  A  K  S  R  G  G  P  G  P

GATTACTATCTCAAAAACTATGAGGATGACATTGTTCGAAGTGATGTTGCCTTAGATAAA  505
 D  Y  Y  L  K  N  Y  E  D  D  I  V  R  S  D  V  A  L  D  K

CAGAAAGGCTGCAAGATTGCCCAGCACCCTGATGTTATGCTGGAGCTCCAAAGGGAGAAG  565
 Q  K  G  C  K  I  A  Q  H  P  D  V  M  L  E  L  Q  R  E  K

GCAGCTCAGATGCATCTGGTTCTTCTAAAGGAGCAATTCTCCAATACTTACAGTAATCTC  625
 A  A  Q  M  H  L  V  L  L  K  E  Q  F  S  N  T  Y  S  N  L

ATATTAACAGCCAGGTCTCTAGACAAACTTTATAACTTTGCTGATTGCTCTGGACTCCAC  685
 I  L  T  A  R  S  L  D  K  L  Y  N  F  A  D  C  S  G  L  H

CTGATATTTGCTCTAAATGCACTGCGTCGTAATCCCAATAACTCCTGGAACAGTTCTAGT  745
 L  I  F  A  L  N  A  L  R  R  N  P  N  N  S  W  N  S  S  S

GCCCTGAGTCTGTTGAAGTACAGCGCCAGCAAAAAGTACAACATTTCTTGGGAACTGGGT  805
 A  L  S  L  L  K  Y  S  A  S  K  K  Y  N  I  S  W  E  L  G

AATGAGCCAAATAACTATCGGACCATGCATGGCCGGGCAGTAAATGGCAGCCAGTTGGGA  865
 N  E  P  N  N  Y  R  T  M  H  G  R  A  V  N  G  S  Q  L  G

AAGGATTACATCCAGCTGAAGAGCCTGTTGCAGCCCATCCGGATTTATTCCAGAGCCAGC  925
 K  D  Y  I  Q  L  K  S  L  L  Q  P  I  R  I  Y  S  R  A  S

TTATATGGCCCTAATATTGGGCGGCCGAGGAAGAATGTCATCGCCCTCCTAGATGGATTC  985
 L  Y  G  P  N  I  G  R  P  R  K  N  V  I  A  L  L  D  G  F

ATGAAGGTGGCAGGAAGTACAGTAGATGCAGTTACCTGGCAACATTGCTACATTGATGGC 1045
 M  K  V  A  G  S  T  V  D  A  V  T  W  Q  H  C  Y  I  D  G

CGGGTGGTCAAGGTGATGGACTTCCTGAAAACTCGCCTGTTAGACACACTCTCTGACCAG 1105
 R  V  V  K  V  M  D  F  L  K  T  R  L  L  D  T  L  S  D  Q

ATTAGGAAAATTCAGAAAGTGGTTAATACATACACTCCAGGAAAGAAGATTTGGCTTGAA 1165
 I  R  K  I  Q  K  V  V  N  T  Y  T  P  G  K  K  I  W  L  E

GGTGTGGTGACCACCTCAGCTGGAGGCACAAACAATCTATCCGATTCCTATGCTGCAGGA 1225
 G  V  V  T  T  S  A  G  G  T  N  N  L  S  D  S  Y  A  A  G

TTCTTATGGTTGAACACTTTAGGAATGCTGGCCAATCAGGGCATTGATGTCGTGATACGG 1285
 F  L  W  L  N  T  L  G  M  L  A  N  Q  G  I  D  V  V  I  R

CACTCATTTTTTGACCATGGATACAATCACCTCGTGGACCAGAATTTTAACCCATTACCA 1345
 H  S  F  F  D  H  G  Y  N  H  L  V  D  Q  N  F  N  P  L  P

GACTACTGGCTCTCTCTCCTCTACAAGCGCCTGATCGGCCCCAAAGTCTTGGCTGTGCAT 1405
 D  Y  W  L  S  L  L  Y  K  R  L  I  G  P  K  V  L  A  V  H

GTGGCTGGGCTCCAGCGGAAGCCACGGCCTGGCCGAGTGATCCGGGACAAACTAAGGATT 1465
 V  A  G  L  Q  R  K  P  R  P  G  R  V  I  R  D  K  L  R  I
```

```
TATGCTCACTGCACAAACCACCACAACCACAACTACGTTCGTGGGTCCATTACACTTTTT      1525
 Y  A  H  C  T  N  H  H  N  H  N  Y  V  R  G  S  I  T  L  F

ATCATCAACTTGCATCGATCAAGAAAGAAAATCAAGCTGGCTGGGACTCTCAGAGACAAG      1585
 I  I  N  L  H  R  S  R  K  K  I  K  L  A  G  T  L  R  D  K

CTGGTTCACCAGTACCTGCTGCAGCCCTATGGGCAGGAGGGCCTAAAGTCCAAGTCAGTG      1645
 L  V  H  Q  Y  L  L  Q  P  Y  G  Q  E  G  L  K  S  K  S  V

CAACTGAATGGCCAGCCCTTAGTGATGGTGGACGACGGGACCCTCCCAGAATTGAAGCCC      1705
 Q  L  N  G  Q  P  L  V  M  V  D  D  G  T  L  P  E  L  K  P

CGCCCCCTTCGGGCCGGCCGGACATTGGTCATCCCTCCAGTCACCATGGGCTTTTTTGTG      1765
 R  P  L  R  A  G  R  T  L  V  I  P  P  V  T  M  G  F  F  V

GTCAAGAATGTCAATGCTTTGGCCTGCCGCTACCGATAAGCTATCCTCACACTCATGGCT      1825
 V  K  N  V  N  A  L  A  C  R  Y  R  *

ACCAGTGGGCCTGCTGGGCTGCTTCCACTCCTCCACTCCAGTAGTATCCTCTGTTTTCAG      1885

ACATCCTAGCAACCAGCCCCTGCTGCCCCATCCTGCTGGAATCAACACAGACTTGCTCTC     1945

CAAAGAGACTAAATGTCATAGCGTGATCTTAGCCTAGGTAGGCCACATCCATCCCAAAGG     2005

AAAATGTAGACATCACCTGTACCTATATAAGGATAAAGGCATGTGTATAGAGCAA          2060
```

Fig. 1b

```
  1 MRVLCAFPEAMPSSNSRPPACLAPGALYLALLLHLSLSSQAGDRRPLPVD  50
                    |    |   | | |     |   |     .
  1 ..................MLLRSKPALPPPLMLLLLGPLGPLSPGALP  30

51 RAAGLKEKTLILLDVSTKNPVRTVNENFLSLQLDPSIIHD.GWLDFLSSK  99
    | |   . . .: ||  |. |.  |. .|||. :|  .: | .| | |
 31 RPA..QAQDVVDLDFFTQEPLHLVSPSFLSVTIDANLATDPRFLILLGSP  78

100 RLVTLARGLSPAFLRFGGKRTDFLQFQNLRNPAKSRGGPGPDYYLKNYED 149
    :| |||||||||:||||| :|||| |    .| |         |:
 79 KLRTLARGLSPAYLRFGGTKTDFLIF....DPKKESTFEERSYWQSQVNQ 124

150 DIVRSDVALDKQKGCKIAQHPDVMLELQREKAAQMHLVLLKEQFSNTYSN 199
    ||          ||       |  . | |  .    .||:| :  : |
125 DI...........CKYGSIPPDVEEKLRLEWPYQEQLLLREHYQKKFKN  162

200 LILTARSLDKLYNFADCSGLHLIFALNALRRNPNNSWNSSSALSLLKYSA 249
     .  |-| || ||-|||| ||| ||||  | .  ||||.|  || | .
163 STYSRSSVDVLYTFANCSGLDLIFGLNALLRTADLQWNSSNAQLLLDYCS 212

250 SKKYNISWELGNEPNNYRTMHGRAVNGSQLGKDYIQLKSLLQPIRIYSRA 299
    || |||||||||||||.:       :||||||.|:|||   ||.   : |
213 SKGYNISWELGNEPNSFLKKADIFINGSQLGEDFIQLHKLLRK.STFKNA 261

300 SLYGPNIGRPRKNVIALLDGFMKVAGSTVDAVTWQHCYIDGRVVKVMDFL 349
    ||||.:|.||:    :| |:| | |  :|-||| | |:.||    |||
262 KLYGPDVGQPRRKTAKMLKSFLKAGGEVIDSVTWHHYYLNGRTATREDFL 311

350 KTRLLDTLSDQIRKIQKVVNTYTPGKKIWLEGVVTTSAGGTNNLSDSYAA 399
    .||       :.|:  .|| .  ||||:||      ||   |||.:||
312 NPDVLDIFISSVQKVFQVVESTRPGKKVWLGETSSAYGGGAPLLSDTFAA 361

400 GFLWLNTLGMLANQGIDVVIRHSFFDHGYNHLVDQNFNPLPDYWLSLLYK 449
    ||:||. ||: | ||:||.| || | ||||:||.||||||||||:|
362 GFMWLDKLGLSARMGIEVVMRQVFFGAGNYHLVDENFDPLPDYWLSLLFK 411

450 RLIGPKVLAVHVAGLQRKPRPGRVIRDKLRIYAHCTNHHNHNYVRGSITL 499
    :|:| |||   | | .|:       |||:| ||||  | | |  :||
412 KLVGTKVLMASVQGSKRR........KLRVYLHCTNTDNPRYKEGDLTL  452

500 FIINLHRSRKKIKLAGTLRDKLVHQYLLQPYGQEGLKSKSVQLNGQPLVM 549
    : ||||    | ::|      .| | .|||.| |  || |||||||| | |
453 YAINLHNVTKYLRLPYPFSNKQVDKYLLRPLGPHGLLSKSVQLNGLTLKM 502

550 VDDGTLPELKPRPLRAGRTLVIPPVTMGFFVVKNVNALACRYR         592
    ||| ||| |  :||| | .| :|  . |||::|   ||
503 VDDQTLPPLMEKPLRPGSSLGLPAFSYSFFVIRNAKVAACI.          543
```

Fig. 2

POLYNUCLEOTIDES AND POLYPEPTIDES ENCODED THEREBY DISTANTLY HOMOLOGOUS TO HEPARANASE

This application is a National Phase of PCT/IL00/00358, filed Jun. 19, 2000, which claims the benefit of priority from U.S. Provisional Application No. 60/140,801, filed Jun. 25, 1999.

FIELD AND BACKGROUND OF THE INVENTION

The present invention relates to novel polynucleotides encoding polypeptides distantly homologous to heparanase, nucleic acid constructs including the polynucleotides, genetically modified cells expressing same, recombinant proteins encoded thereby and which may have heparanase or other glycosyl hydrolase activity, antibodies recognizing the recombinant proteins, oligonucleotides and oligonucleotide analogs derived from the polynucleotides and ribozymes including same.

Citation or identification of any reference in this application shall not be construed as an admission that such reference is available as prior art to the present invention.

Glycosaminoglycans (GAGs)

GAGs are polymers of repeated disaccharide units consisting of uronic acid and a hexosamine. Biosynthesis of GAGs except hyaluronic acid is initiated from a core protein. Proteoglycans may contain several GAG side chains from similar or different families. GAGs are synthesized as homopolymers which may subsequently be modified by N-deacetylation and N-sulfation, followed by C5-epimerization of glucuronic acid to iduronic acid and O-sulfation. The chemical composition of GAGs from various tissues varies highly.

The natural metabolism of GAGs in animals is carried out by hydrolysis. Generally, the GAGs are degraded in a two step procedure. First the proteoglycans are internalized in endosomes, where initial depolymerization of the GAG chain takes place. This step is mainly hydrolytic and yields oligosaccharides. Further degradation is carried out after fusion with lysosome, where desulfation and exolytic depolymerization to monosaccharides take place (42).

The only mammalian GAG degrading endolytic enzymes characterized so far are the hyaluronidases. The hyaluronidases are a family of 1–4 endoglucosaminidases that depolymerize hyaluronic acid and chondroitin sulfate. The cDNAs encoding sperm associated PH-20 (Hyal3), and the lysosomal hyaluronidases Hyal 1 and Hyal2 were cloned and published (27). These enzymes share an overall homology of 40% and have different tissue specificities, cellular localizations and PH optima.

Exolytic hydrolases are better characterized, among which are glucoronidase, α-L-iduronidase, and β-N-acetylglucosaminidase. In addition to hydrolysis of the glycosidic bond of the polysaccharide chain, GAG degradation involves desulfation, which is catalyzed by several lysosomal sulfatases such as N-acetylgalactosamine sulfatase, iduronate-2-sulfatase and heparin sulfamidase. Deficiency in any of lysosomal GAG degrading enzymes results in a lysosomal storage disease, mucopolysaccharidosis.

Glycosyl Hydrolases:

Glycosyl hydrolases are a widespread group of enzymes that hydrolyze the o-glycosidic bond between two or more carbohydrates or between a carbohydrate and a noncarbohydrate moiety. The enzymatic hydrolysis of glycosidic bond occurs by using major one or two mechanisms leading to overall retention or inversion of the anomeric configuration. In both mechanisms catalysis involves two residues: a proton donor and a nucleophile. Glycosyl hydrolyses have been classified into 58 families based on amino acid similarities. The glycosyl hydrolyses from families 1, 2, 5, 10, 17, 30, 35, 39 and 42 act on a large variety of substrates, however, they all hydrolyze the glycosidic bond in a general acid catalysis mechanism, with retention of the anomeric configuration. The mechanism involves two glutamic acid residues, which are the proton donors and the nucleophile, with an aspargine always preceding the proton donor. Analyses of a set of known 3D structures from this group revealed that their catalytic domains, despite the low level of sequence identity, adopt a similar (α/β) 8 fold with the proton donor and the nucleophile located at the C-terminal ends of strands β4 and β7, respectively. Mutations in the functional conserved amino acids of lysosomal glycosyl hydrolases were identified in lysosomal storage diseases.

Lysosomal glycosyl hydrolases including β-glucuronidase, β-manosidase, β-glucocerebrosidase, β-galactosidase and α-L-iduronidase, are all exo-glycosyl hydrolases, belong to the GH-A clan and share a similar catalytic site. However, many endo-glucanases from various organisms, such as bacterial and fungal xylenases and cellulases share this catalytic domain (1).

Heparan Sulfate Proteoglycans (HSPGs)

HSPGs are ubiquitous macromolecules associated with the cell surface and extracellular matrix (ECM) of a wide range of cells of vertebrate and invertebrate tissues (3–7). The basic HSPG structure consists of a protein core to which several linear heparan sulfate chains are covalently attached. The polysaccharide chains are typically composed of repeating hexuronic and D-glucosamine disaccharide units that are substituted to a varying extent with N- and O-linked sulfate moieties and N-linked acetyl groups (3–7). Studies on the involvement of ECM molecules in cell attachment, growth and differentiation revealed a central role of HSPGs in embryonic morphogenesis, angiogenesis, metastasis, neurite outgrowth and tissue repair (3–7). The heparan sulfate (HS) chains, which are unique in their ability to bind a multitude of proteins, ensure that a wide variety of effector molecules cling to the cell surface (6–8). HSPGs are also prominent components of blood vessels (5). In large vessels they are concentrated mostly in the intima and inner media, whereas in capillaries they are found mainly in the subendothelial basement membrane where they support proliferating and migrating endothelial cells and stabilize the structure of the capillary wall. The ability of HSPGs to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of HS may therefore result in disassembly, of the subendothelial ECM and hence may play a decisive role in extravasation of normal and malignant blood-borne cells (9–11). HS catabolism is observed in inflammation, wound repair, diabetes, and cancer metastasis, suggesting that enzymes which degrade HS play important roles in pathologic processes.

Heparanase

Heparanase is a glycosylated enzyme that is involved in the catabolism of certain glycosaminoglycans. It is an endoglucouronidase that cleaves heparan sulfate at specific intrachain sites (12–15). Interaction of T and B lymphocytes, platelets, granulocytes, macrophages and mast cells with the subendothelial extracellular matrix (ECM) is associated with degradation of heparan sulfate by heparanase activity (16). Connective tissue activating peptide III (CTAP), a c-chemokine, was found to have heparanase-like activity. Placenta heparanase acts as an adhesion molecule or as a degradative enzyme depending on the pH of the microenvironvent (17).

Heparanase is released from intracellular compartments. (e.g., lysosomes, specific granules) in response to various activation signals (e.g., thrombin, calcium ionophores, immune complexes, antigens and mitogens), suggesting its regulated involvement in inflammation and cellular immunity responses (16).

It was also demonstrated that heparanase can be readily released from human neutrophils by 60 minutes incubation at 4 C in the absence of added stimuli (18).

Gelatinase, another ECM degrading enzyme which is found in tertiary granules of human neutrophils with heparanase, is secreted from the neutrophils in response to phorbol 12-myristate 13-acetate (PMA) treatment (19–20).

In contrast, various tumor cells appear to express and secrete heparanase in a constitutive manner in correlation with their metastatic potential (21).

Degradation of heparan sulfate by heparanase results in the release of heparin-binding growth factors, enzymes and plasma proteins that are sequestered by heparan sulfate in basement membranes, extracellular matrices and cell surfaces (22–23).

Heparanase activity has been described in a number of cell types including cultured skin fibroblasts, human neutrophils, activated rat T-lymphocytes, normal and neoplastic murine B-lymphocytes, human monocytes and human umbilical vein endothelial cells, SK hepatoma cells, human placenta and human platelets.

A procedure for purification of natural heparanase was reported for SK hepatoma cells and human placenta (U.S. Pat. No. 5,362,641) and for human platelets derived enzymes (62).

Cloning and Expression of the Heparanase Gene

A purified fraction of heparanase isolated from human hepatoma cells was subjected to tryptic digestion. Peptides were separated by high pressure liquid chromatography (HPLC) and micro sequenced. The sequence of one of the peptides was used to screen data bases for homology to the corresponding back translated DNA sequence. This procedure led to the identification of a clone containing an insert of 1020 base pairs (bp) which included an open reading frame of 963 bp followed by 27 bp of 3' untranslated region and a poly A tail. The new gene was designated hpa. Cloning of the missing 5' end of hpa was performed by Marathon RACE from placenta cDNA composite. The joined hpa cDNA (also referred to as phpa) fragment contained an open reading frame, which encodes a polypeptide of 543 amino acids with a calculated molecular weight of 61,192 daltons (2). The cloning procedures are described in length in U.S. patent application Ser. Nos. 08/922,170, 09/109,386, and 09/258,892, the latter is a continuation-in-part of PCT/US98/17954, filed Aug. 31, 1998, all of which are incorporated herein by reference.

The genomic locus which encodes heparanase spans about 40 kb. It is composed of 12 exons separated by 11 introns and is localized on human chromosome 4.

The ability of the hpa gene product to catalyze degradation of heparan sulfate (HS) in vitro was examined by expressing the entire open reading frame of hpa in High five and Sf21 insect cells, and the mammalian human 293 embryonic kidney cell line expression systems. Extracts of infected or transfected cells were assayed for heparanase catalytic activity. For this purpose, cell lysates were incubated with sulfate labeled, ECM-derived HSPG (peak I), followed by gel filtration analysis (Sepharose 6B) of the reaction mixture. While the substrate alone consisted of high molecular weight material, incubation of the HSPG substrate with lysates of cells infected or transfected with hpa containing vectors resulted in a complete conversion of the high molecular weight substrate into low molecular weight labeled heparan sulfate degradation fragments (see, for example, U.S. patent application Ser. No. 09/071,618, which is incorporated herein by reference.

In other experiments, it was demonstrated that the heparanase enzyme expressed by cells infected with a pFhpa virus is capable of degrading HS complexed to other macromolecular constituents (e.g., fibronectin, laminin, collagen) present in a naturally produced intact ECM (see U.S. patent application Ser. No. 09/109,386, which is incorporated herein by reference), in a manner similar to that reported for highly metastatic tumor cells or activated cells of the immune system (7, 8).

Preferential Expression of the hpa Gene in Human Breast and Hepatocellular Carcinomas Semi-quantitative RT-PCR was applied to evaluate the expression of the hpa gene by human breast carcinoma cell lines exhibiting different degrees of metastasis. A marked increase in hpa gene expression is observed which correlates to metastatic capacity of non-metastatic MCF-7 breast carcinoma, moderately metastatic MDA 231 and highly metastatic MDA 435 breast carcinoma cell lines. Significantly, the differential pattern of the hpa gene expression correlated with the pattern of heparanase activity.

Expression of the hpa gene in human breast carcinoma was demonstrated by in situ hybridization to archival paraffin embedded human breast tissue. Hybridization of the heparanase antisense riboprobe to invasive duct carcinoma tissue sections resulted in a massive positive staining localized specifically to the carcinoma cells. The hpa gene was also expressed in areas adjacent to the carcinoma showing fibrocystic changes. Normal breast tissue derived from reduction mammoplasty failed to express the hpa transcript. High expression of the hpa gene was also observed in tissue sections derived from human hepatocellular carcinoma specimens but not in normal adult liver tissue. Furthermore, tissue specimens derived from adenocarcinoma of the ovary, squamous cell carcinoma of the cervix and colon adenocarcinoma exhibited strong staining with the hpa RNA probe, as compared to a very low staining of the hpa mRNA in the respective non-malignant control tissues (2).

A preferential expression of heparanase in human tumors versus the corresponding normal tissues was also noted by immunohistochemical staining of paraffin embedded sections with monoclonal anti-heparanase antibodies. Positive cytoplasmic staining was found in neoplastic cells of the colon carcinoma and in dysplastic epithelial cells of a tubulovillous adenoma found in the same specimen while there was little or no staining of the normal looking colon epithelium located away from the carcinoma. Of particular significance was an intense immunostaining of colon adenocarcinoma cells that had metastasized into the liver, as compared to the surrounding normal liver tissue.

Latent and Active Forms of the Heparanase Protein

The apparent molecular size of the recombinant enzyme produced in the baculovirus expression system was about 65 kDa. This heparanase polypeptide contains 6 potential N-glycosylation sites. Following deglycosylation by treatment with peptide N-glycosidase, the protein appeared as a 57 kDa band. This molecular weight corresponds to the deduced molecular mass (61,192 daltons) of the 543 amino acid polypeptide encoded by the full length hpa cDNA after cleavage of the predicted 3 kDa signal peptide. No further reduction in the apparent size of the N-deglycosylated protein was observed following concurrent O-glycosidase and neuramimidase treatment. Deglycosylation had no detectable effect on enzymatic activity.

Unlike the baculovirus enzyme, expression of the full length heparanase polypeptide in mammalian cells (e.g., 293 kidney cells, CHO) yielded a major protein of about 50 kDa and a minor about 65 kDa protein in cell lysates. Preferential release of the about 65 kDa form into the culture medium was noted in some of the transfected CHO clones. Comparison of the enzymatic activity of the two forms, using a semi-quantitative gel filtration assay, revealed that the 50 kDa enzyme is about 100-fold more active than the 65 kDa form. A similar difference was observed when the specific activity of the recombinant 65 kDa baculovirus enzyme was compared to that of the 50 kDa heparanase preparations purified from human platelets, SK-hep-1 cells, or placenta. These results suggest that the 50 kDa protein is a mature processed form of a latent heparanase precursor. Amino terminal sequencing of the platelet heparanase indicated that cleavage occurs between amino acids $glu^{157}$-$lys^{158}$. As indicated by the hydropathic plot of heparanase, this site is located within a hydrophillic peak which is likely to be exposed and hence accessible to proteases.

Involvement of Heparanase in Tumor Cell Invasion and Metastasis

Circulating tumor cells arrested in the capillary beds often attach at or near the intercellular junctions between adjacent endothelial cells. Such attachment of the metastatic cells is followed by rupture of the junctions, retraction of the endothelial cell borders and migration through the breach in the endothelium toward the exposed underlying base membrane (BM) (24). Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase, etc.) are thought to be involved in degradation of BM (25). Among these enzymes is heparanase that cleaves HS at specific intrachain sites (16, 11). Expression of a HS degrading heparanase was found to correlate with the metastatic potential of mouse lymphoma (26), fibrosarcoma and melanoma (21) cells. Moreover, elevated levels of heparanase were detected in sera from metastatic tumor bearing animals and melanoma patients (21) and in tumor biopsies of cancer patients (12).

The inhibitory effect of various non-anticoagulant species of heparin on heparanase was examined in view of their potential use in preventing extravasation of blood-borne cells. Treatment of experimental animals with heparanase inhibitors markedly reduced (>90%) the incidence of lung metastases induced by B16 melanoma, Lewis lung carcinoma and mammary adenocarcinoma cells (12, 13, 28). Heparin fractions with high and low affinity to anti-thrombin III exhibited a comparable high anti-metastatic activity, indicating that the heparanase inhibiting activity of heparin, rather than its anticoagulant activity, plays a role in the anti-metastatic properties of the polysaccharide (12).

The direct role of heparanase in cancer metastasis was demonstrated by two experimental systems. The murine T-lymphoma cell line Eb has no detectable heparanase activity. Whether the introduction of the hpa gene into Eb cells would confer a metastatic behavior on these cells was investigated. To this purpose, Eb cells were transfected with a full length human hpa cDNA. Stable transfected cells showed high expression of the heparanase mRNA and enzyme activity. These hpa and mock transfected Eb cells were injected subcutaneously into DBA/2 mice and mice were tested for survival time and liver metastases. All mice (n=20) injected with mock transfected cells survived during the first 4 weeks of the experiment, while 50% mortality was observed in mice inoculated with Eb cells transfected with the hpa cDNA. The liver of mice inoculated with hpa transfected cells was infiltrated with numerous Eb lymphoma cells, as was evident both by macroscopic evaluation of the liver surface and microscopic examination of tissue sections. In contrast, metastatic lesions could not be detected by gross examination of the liver of mice inoculated with mock transfected control Eb cells. Few or no lymphoma cells were found to infiltrate the liver tissue. In a different model of tumor metastasis, transient transfection of the heparanase gene into low metastatic B16-F1 mouse melanoma cells followed by i.v. inoculation, resulted in a 4- to 5-fold increase in lung metastases.

Finally, heparanase externally adhered to B16-F1 melanoma cells increased the level of lung metastases in C57BL mice as compared to control mice (see U.S. patent application Ser. No. 09/260,037, entitled INTRODUCING A BIOLOGICAL MATERIAL INTO A PATIENT, which is a continuation in part of U.S. patent application Ser. No. 09/140,888, and is incorporated herein by reference.

Possible Involvement of Heparanase in Tumor Angiogenesis

Fibroblast growth factors are a family of structurally related polypeptides characterized by high affinity to heparin (29). They are highly mitogenic for vascular endothelial cells and are among the most potent inducers of neovascularization (29–30). Basic fibroblast growth factor (bFGF) has been extracted from a subendothelial ECM produced in vitro (31) and from basement membranes of the cornea (32), suggesting that ECM may serve as a reservoir for bFGF. Immunohistochemical staining revealed the localization of bFGF in basement membranes of diverse tissues and blood vessels (23). Despite the ubiquitous presence of bFGF in normal tissues, endothelial cell proliferation in these tissues is usually very low, suggesting that bFGF is somehow sequestered from its site of action. Studies on the interaction of bFGF with ECM revealed that bFGF binds to HSPG in the ECM and can be released in an active form by HS degrading enzymes (33, 32, 34). It was demonstrated that heparanase activity expressed by platelets, mast cells, neutrophils, and lymphoma cells is involved in release of active bFGF from ECM and basement membranes (35), suggesting that heparanase activity may not only function in cell migration and invasion, but may also elicit an indirect neovascular response. These results suggest that the ECM HSPG provides a natural storage depot for bFGF and possibly other heparin-binding growth promoting factors (36, 37). Displacement of bFGF from its storage within basement membranes and ECM may therefore provide a novel mechanism for induction of neovascularization in normal and pathological situations.

Recent studies indicate that heparin and HS are involved in binding of bFGF to high affinity cell surface receptors and in bFGF cell signaling (38, 39). Moreover, the size of HS required for optimal effect was similar to that of HS fragments released by heparanase (40). Similar results were obtained with vascular endothelial cells growth factor (VEGF) (41), suggesting the operation of a dual receptor mechanism involving HS in cell interaction with heparin-binding growth factors. It is therefore proposed that restriction of endothelial cell growth factors in ECM prevents their systemic action on the vascular endothelium, thus maintaining a very low rate of endothelial cells turnover and vessel growth. On the other hand, release of bFGF from storage in ECM as a complex with HS fragment, may elicit localized endothelial cell proliferation and neovascularization in processes such as wound healing, inflammation and tumor development (36, 37).

The Involvement of Heparanase in other Physiological Processes and its Potential Therapeutic Applications Apart from its involvement in tumor cell metastasis, inflammation and autoimmunity, mammalian heparanase may be applied to modulate bioavailability of heparin-binding growth factors; cellular responses to heparin-binding growth factors (e.g., bFGF, VEGF) and cytokines (IL-8) (44, 41); cell interaction with plasma lipoproteins (49); cellular susceptibility to certain viral and some bacterial and protozoa infections (45–47); and disintegration of amyloid plaques (48).

Viral Infection: The presence of heparan sulfate on cell surfaces have been shown to be the principal requirement for the binding of Herpes Simplex (45) and Dengue (46) viruses to cells and for subsequent infection of the cells. Removal of the cell surface heparan sulfate by heparanase may therefore abolish virus infection. In fact, treatment of cells with bacterial heparitinase (degrading heparan sulfate) or heparinase (degrading heparan) reduced the binding of two related animal herpes viruses to cells and rendered the cells at least partially resistant to virus infection (45). There are some indications that the cell surface heparan sulfate is also involved in HIV infection (47).

Neurodegenerative diseases: Heparan sulfate proteoglycans were identified in the prion protein amyloid plaques of Genstmann-Straussler Syndrome, Creutzfeldt-Jakob disease and Scrape (48). Heparanase may disintegrate these amyloid plaques which are also thought to play a role in the pathogenesis of Alzheirmer's disease.

Restenosis and Atherosclerosis: Proliferation of arterial smooth muscle cells (SMCs) in response to endothelial injury and accumulation of cholesterol rich lipoproteins are basic events in the pathogenesis of atherosclerosis and restenosis (50). Apart from its involvement in SMC proliferation as a low affinity receptor for heparin-binding growth factors, HS is also involved in lipoprotein binding, retention and uptake (51). It was demonstrated that HSPG and lipoprotein lipase participate in a novel catabolic pathway that may allow substantial cellular and interstitial accumulation of cholesterol rich lipoproteins (49). The latter pathway is expected to be highly atherogenic by promoting accumulation of apoB and apoE rich lipoproteins (e.g., LDL, VLDL, chylomicrons), independent of feed back inhibition by the cellular cholesterol content. Removal of SMC HS by heparanase is therefore expected to inhibit both SMC proliferation and lipid accumulation and thus may halt the progression of restenosis and atherosclerosis.

Pulmonary Diseases:

The data obtained from the literature suggests a possible role for GAGs degrading enzymes, such as, but not limited to, heparanases, connective tissue activating peptide, heparinases, hyluronidases, sulfatases and chondroitinases, in reducing the viscosity of sinuses and airway secretions with associated implications on curtailing the rate of infection and inflammation. The sputum from CF patients contains at least 3% GAGs, thus contributing to its volume and viscous properties. Recombinant heparanase has been shown to reduce viscosity of sputum of CF patients (see, U.S. patent application Ser. No. 09/046,475).

In summary, heparanase may thus prove useful for conditions such as wound healing, angiogenesis, restenosis, atherosclerosis, inflammation, neurodegenerative diseases and viral infections. Mammalian heparanase can be used to neutralize plasma heparin, as a potential replacement of protamine. Anti-heparanase antibodies may be applied for immunodetection and diagnosis of micrometastases, autoimmune lesions and renal failure in biopsy specimens, plasma samples, and body fluids.

There is thus a widely recognized need for, and it would be highly advantageous to have, additional molecules with glycosyl hydrolase activity, because such molecules may exhibit greater specific activity toward certain substrates or different substrate specificity than the known heparanase.

SUMMARY OF THE INVENTION

According to one aspect of the present invention there is provided an isolated nucleic acid comprising a polynucleotide hybridizable with SEQ ID NOs:1, 4, 6 or portions thereof at 68° C. in 6×SSC, 1% SDS, 5× Denharts, 10% dextran sulfate, 100 µg/ml salmon sperm DNA, and $^{32}$p labeled probe and wash at 68° C. with 3×SSC and 0.1% SDS.

According to another aspect of the present invention there is provided an isolated nucleic acid comprising a polynucleotide hybridizable with SEQ ID NOs:1, 4, 6 or portions thereof at 68° C. in 6×SSC, 1% SDS, 5× Denharts, 10% dextran sulfate, 100 µg/ml salmon sperm DNA, and $^{32}$p labeled probe and wash at 68° C. with 1×SSC and 0.1% SDS.

According to still another aspect of the present invention there is provided an isolated nucleic acid comprising a polynucleotide hybridizable with SEQ ID NOs:1, 4, 6 or portions thereof at 68° C. in 6×SSC, 1% SDS, 5× Denharts, 10% dextran sulfate, 100 µg/ml salmon sperm DNA, and $^{32}$p labeled probe and wash at 68° C. with 0.1×SSC and 0.1% SDS.

According to yet another aspect of the present invention there is provided an isolated nucleic acid comprising a polynucleotide at least 60% identical with SEQ ID NOs:1, 4, 6 or portions thereof as determined using the Bestfit procedure of the DNA sequence analysis software package developed by the Genetic Computer Group (GCG) at the university of Wisconsin (gap creation penalty −50, gap extension penalty −3).

According to still another aspect of the present invention there is provided an isolated nucleic acid comprising a polynucleotide encoding a polypeptide being at least 60% homologous with SEQ ID NOs:3, 5, 7 or portions thereof as determined using the Bestfit procedure of the DNA sequence analysis software package developed by the Genetic Computer Group (GCG) at the university of Wisconsin (gap creation penalty −50, gap extension penalty −3).

According to further features in preferred embodiments of the invention described below, the polynucleotide is as set forth in SEQ ID NOs:1, 4, 6 or portions thereof.

According to an additional aspect of the present invention there is provided a recombinant protein comprising a polypeptide encoded by the polynucleotides herein described.

According to yet an additional aspect of the present invention there is provided a recombinant protein comprising a polypeptide at least 60% homologous with SEQ ID NOs:3, 5, 7 or portions thereof as determined using the Bestfit procedure of the DNA sequence analysis software package developed by the Genetic Computer Group (GCG) at the university of Wisconsin (gap creation penalty −50, gap extension penalty −3).

According to further features in preferred embodiments of the invention described below, the polypeptide is as set fourth in SEQ ID NOs:3, 5, 7 or portions thereof.

According to still an additional aspect of the present invention there is provided a nucleic acid construct comprising the isolated nucleic acid herein described.

According to a further aspect of the present invention there is provided a nucleic acid construct comprising a polynucleotide encoding the recombinant protein herein described.

According to still a further aspect of the present invention there is provided a host cell comprising a polynucleotide or construct and/or expressing a recombinant protein as herein described.

According to yet a further aspect of the present invention there is provided an antisense oligonucleotide or nucleic acid construct comprising a polynucleotide or a polynucleotide analog of at least 10 bases being hybridizable in vivo, under physiological conditions, with (i) a portion of a polynucleotide strand encoding a polypeptide at least 60% homologous with SEQ ID NOs:3, 5, 7 or portions thereof as determined using the Bestfit procedure of the DNA sequence analysis software package developed by the Genetic Computer Group (GCG) at the university of Wisconsin (gap creation penalty −50, gap extension penalty −3); or (ii) a portion of a polynucleotide strand at least 60% identical with SEQ ID NOs:1, 4, 6 or portions thereof as determined using the Bestfit procedure of the DNA sequence analysis software package developed by the Genetic Computer Group (GCG) at the university of Wisconsin (gap creation penalty −50, gap extension penalty −3).

According to another aspect of the present invention there is provided a ribozyme comprising the antisense oligonucleotide herein described and a ribozyme sequence.

The present invention provides polynucleotides and polypeptides belonging to a class of asp-glu glycosyl hydrolases of the GH-A clan, probably, based on homology to heparanase, GAG degrading enzymes.

BRIEF DESCRIPTION OF THE DRAWINGS

The invention is herein described, by way of example only, with reference to the accompanying drawings, wherein:

FIG. 1 shows the nucleotide sequence (SEQ ID NOs:1–2) and the deduced amino acid sequence (SEQ ID NOs:2–3) of hnhp1;

FIG. 2 is a comparison of the deduced amino acid sequences of hnhp1 (SEQ ID NOs:2–3) and of heparanase (SEQ ID NO:9). Comparison was performed using the Gap program of the GCG package (gap creation penalty −50, gap extension penalty −3);

DESCRIPTION OF THE PREFERRED EMBODIMENTS

Figure 3:
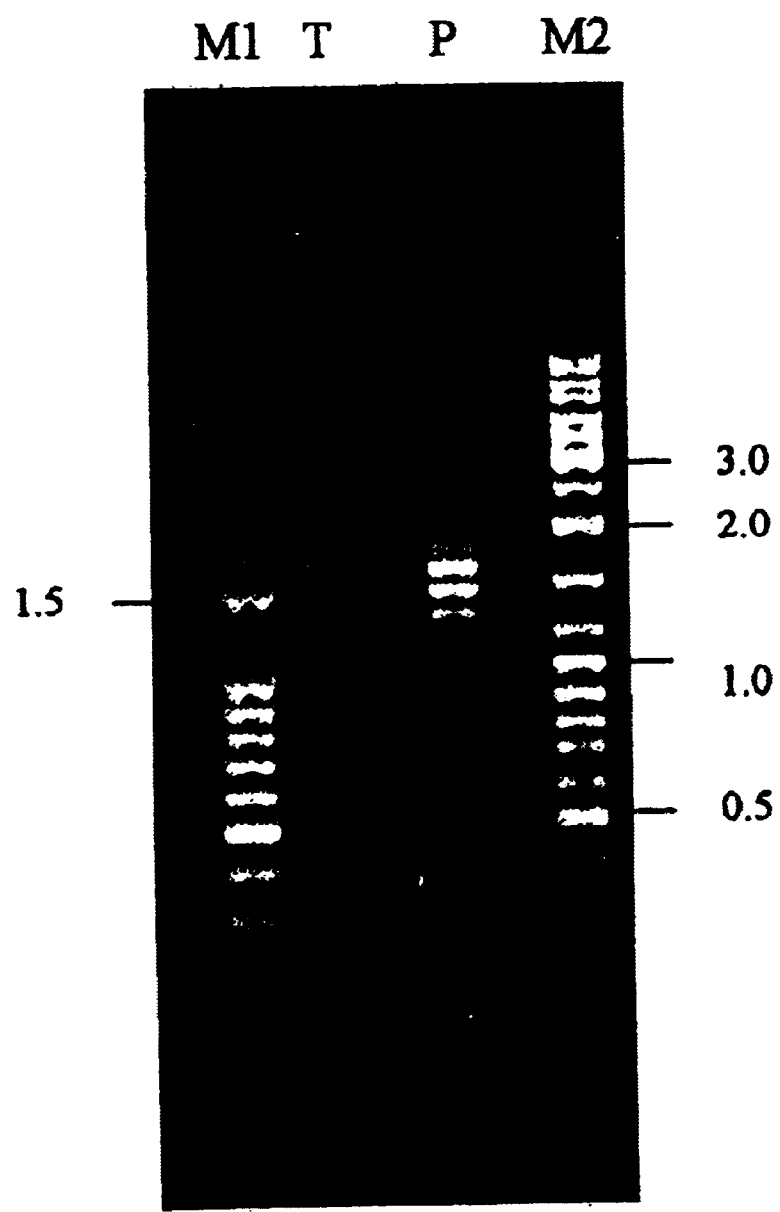
FIG. 3 illustrates variability of hnhp1 transcripts. Hnhp1 was amplified from placenta and from testis marathon ready cDNA libraries, using the gene specific primers pn9-312u (SEQ ID NO:14) and hn11-230, (SEQ ID NO:11)

The present invention is of novel polynucleotides encoding polypeptides distantly homologous to heparanase, nucleic acid constructs including the polynucleotides, genetically modified cells expressing same, recombinant proteins encoded thereby and which may have heparanase or other glycosyl hydrolase activity, antibodies recognizing the recombinant proteins, oligonucleotides and oligonucleotide analogs derived from the polynucleotides and ribozymes including same.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various, ways. Also, it is to be understood that the phraseology and terminology employed herein is for the purpose of description and should not be regarded as limiting.

Figure 5:
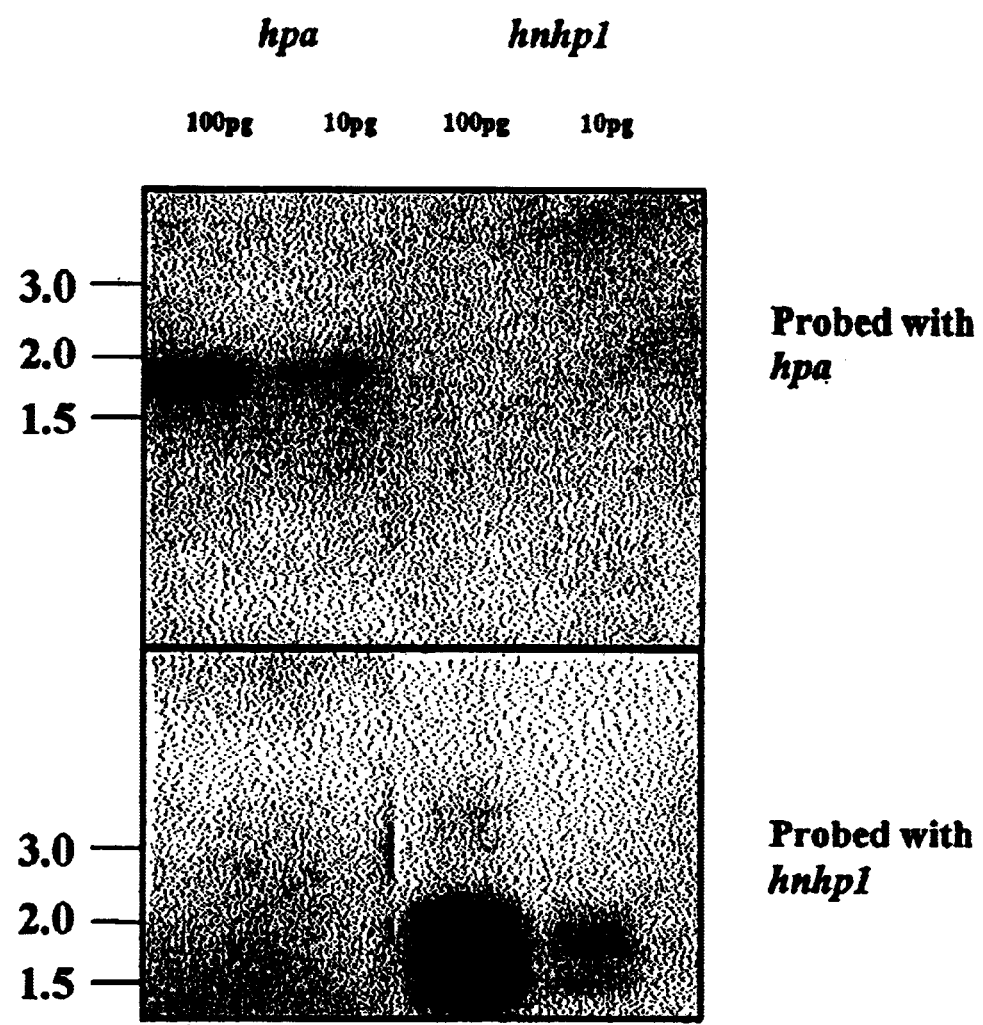
FIG. 5 illustrates cross hybridization between hpa and hnhp1. Hpa was amplified by PCR from marathon ready placenta cDNA library. Hnhp1 was amplified from testis marathon ready cDNA library. PCR products were run on agarose gel in duplicates and transferred to a nylon membrane. One membrane was probed with $^{32}$p labeled hpa cDNA and the other with hnhp1, clone pn9.

While reducing the present invention to practice the human EST database was screened for homologous sequences using the entire amino acid sequence of human heparanase (SEQ ID NO:9). A distantly homologous fragment was pooled out, accession number AI222323, IMAGE clone number 1843155 from Soares_NFL_T_GBC_S1 *Homo Sapiens* cDNA library prepared from testis B-cells and fetal lungs. The clone contained an insert of 560 bp (SEQ ID NO:23) of which the 3' region was homologous to the human hpa gene encoding human heparanase. Primers derived from the newly identified clone were used to isolate several cDNAs including several open reading frames which reflect in frame alternative splicing, the longest of which, pn6, appears in FIG. 1 (SEQ ID NOs:1, 2 and 3) is 2060 nucleotide long and it contains an open reading frame of 1776 nucleotides, which encodes a polypeptide of 592 amino acids, with a calculated molecular weight of 66.5 kDa. The newly cloned gene was designated hnhp1. Two shorter forms, pn9 and pn5 and their deduced amino acid sequences are set forth in SEQ ID NOs:4 and 6 and SEQ ID NO:5 and 7, respectively, and are further described in the Examples section that follows. Comparison between the amino acid sequence of hnhp1 and heparanase is shown in FIG. 3. The homology between the two proteins is 52.8% or 55.3%, depending on the software employed. No cross hybridzation was detected between hpa and hnhp1, even under very moderate wash conditions (FIG. 5). Zoo blot analysis demonstrated that the hnhp1 gene and other related genes, perhaps forming a new gene family, are present in genomes of other organisms including mammals and avians. The chromosome localization of hnhp1 was determined using G3 radiation hybrid panel to be on human chromosome 10, next to the marker SHGC-57721. The results also indicated a possibility of a second copy of the gene or of a related gene. The hnhp1 gene is expressed in low levels in lymph nodes, spleen, colon and ovary; in slightly higher levels in prostate and small intestine; and in yet more pronouced level in testis. No expression was detected under the assay employed in bone marrow, liver, thymus, tonsil or leukocytes. Screening of the mouse EST database with the amino acid sequence of heparanase as well as of hnhp1 pooled out a mouse EST clone (clone 1378452 accession number AI019269 from mouse thymus, SEQ ID NO:8). However, this clone includes two frame shift mutations which hamper its open reading frame.

The overall homology between the amino acid sequence of hnhp1 and heparanase suggest that these two proteins share similar function. The homology between the two proteins is concentrated at several regions. These may represent functional domains of the protein. The variability may suggest potential difference in substrate recognition, cellular localization and parameters of activity.

Despite the lack of an overall homology between the heparanase and other glycosyl hydrolases, the amino acid couple asp-glu (NE, SEQ ID NO:13), which is characteristic of the proton donor of glycosyl hydrolyses of the GH-A clan, was found at positions 224, 225 of heparanase. As in other clan members, this NE couple is located at the end of a β strand. As shown in FIG. 2, the region surrounding the NE couple is conserved in the predicted amino acid sequence of hnhp1. This suggests that hnhp1 product is a glycosyl hydrolase. This definition may include any polysaccharide degrading enzyme, either exo or endo glycosidase and based on the similarity to heparanase it is likely that it encodes a GAG degrading enzyme.

Figure 6:
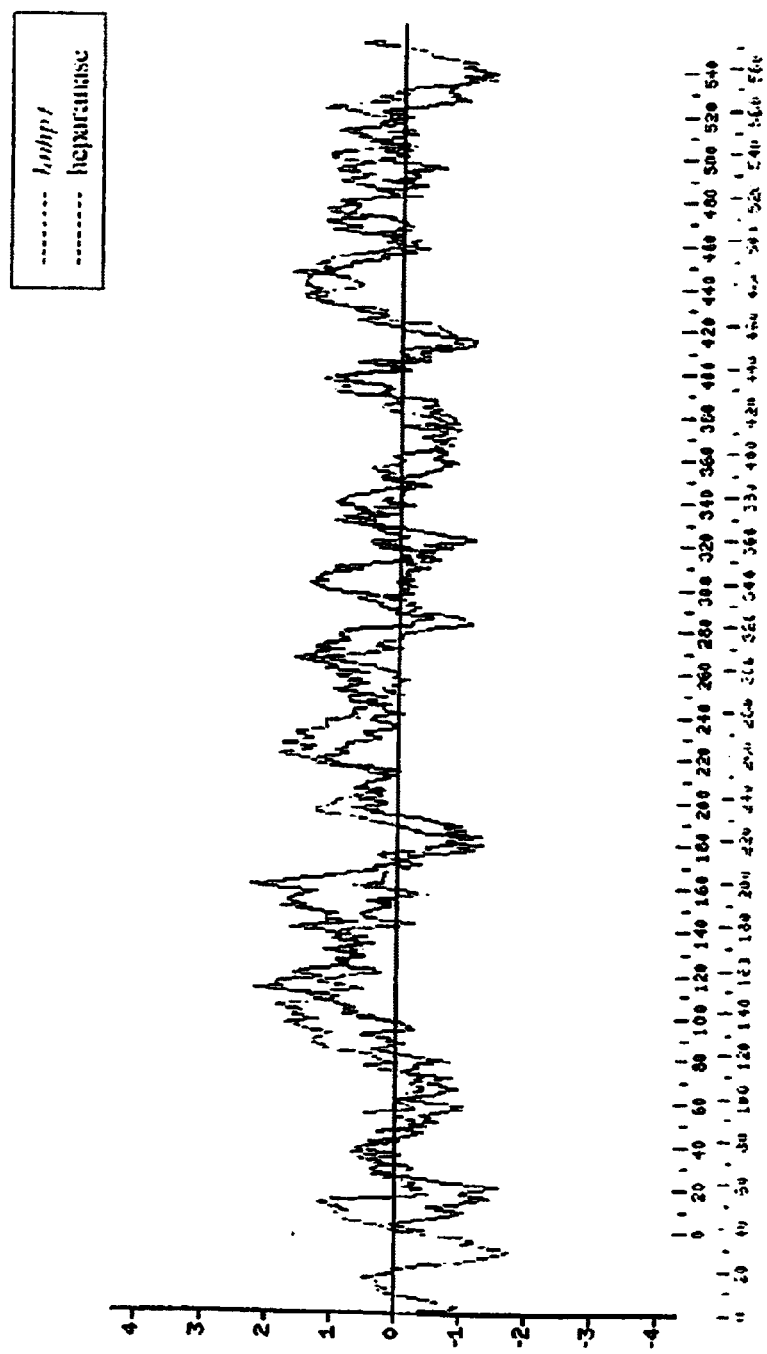
FIG. 6 is a comparison of the hydropathic profiles of heparanase and hnhp1. The curves were calculated according to the Kyte and Dulittle method over a window of 17 amino acids.
Figure 7:
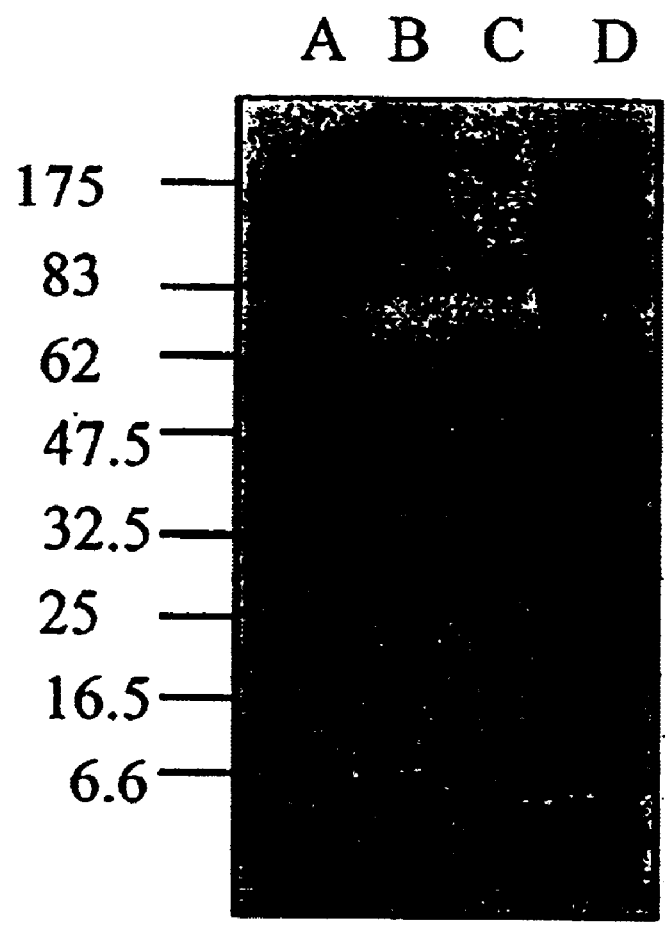
FIG. 7 shows a Western blot analysis of recombinant hnhp1 expressed in human embryonal kidney 293 cells. A—control heparanase-FLAG precursor, B-D—293 cells trasfected with a control pSI vector (B), pSI-pn6 (C) and pSI-pn9 (D). Cell extracts were separated by SDS-PAGE, transferred onto Immobilon-P nylon membrane (Millipore). Membrane was incubated with anti-FLAG Flag antibody 1:1000 (Kodak anti Flag M2 cat: IB13025).

In addition, superimposition of the hydropathic profiles of heparanase and hnhp1 (FIG. 6) indicates an overlapping pattern along the proteins. The amino acid sequence characteristic of glycosyl hydrolases is located within a hydrophilic peak and at the same position in the aligned proteins. A remarkable difference in the hydropathic pattern is noticed around amino acids 157, 158 of heparanase, which constitute the processing site of the enzyme. While in heparanase, this site is located at the tip of a hydrophilic peak, the equivalent region of hnhp1 is rather not hydrophilic. The peak around amino acid 110 of heparanase appears also, around amino acid 130 of hnhp1. Cleavage of heparanase at this region was shown to result in enzyme activation. The equivalent region of hnhp1 might be a potential processing site.

Heparanase has a potential signal peptide at the N-terminus of the 67 kDa form. The homology between the two proteins is low at the N-termini and no signal peptide was identified in hnhp1 polypeptide.

According to one aspect of the present invention there is provided an isolated nucleic acid comprising a polynucleotide hybridizable with SEQ ID NOs:1, 4, 6 or portions thereof at 68° C. in 6×SSC, 1% SDS, 5× Denharts, 10% dextran sulfate, 100 μg/ml salmon sperm DNA, and $^{32}$p labeled probe and wash at 68° C. with 3×SSC, 1×SSC or 0.1×SSC and 0.1% SDS.

As used herein in the specification and in the claims section that follows, the term "portion" or "portions" refer to a consequtive stretch of nucleic or amino acids. Such a portion may include, for example, at least 90 nucleotides (equivalent to at least 30 amino acids), at least 120 nucleotides (equivalent to at least 40 amino acids), at least 150 nucleotides (equivalent to at least 50 amino acids), at least 180 nucleotides. (equivalent to at least 60 amino acids), at least 210 nucleotides (equivalent to at least 70 amino acids), at least 300 nucleotides (equivalent to at least 100 amino acids), at least 600 nucleotides (equivalent to at least 200 amino acids), at least 900 nucleotides (equivalent to at least 300 amino acids), at least 1,200 nucleotides (equivalent to at least 400 amino acids), at least 1,500 nucleotides (equivalent to at least 500 amino acids), or more.

According to another aspect of the present invention there is provided an isolated nucleic acid comprising a polynucleotide at least 60%, preferably at least 65%, more preferably at least 70%, still preferably at least 75%, yet preferably at least 80%, more preferably at least 85%, more preferably at least 90%, most preferably at least 95%–100%, identical with SEQ ID NOs:1, 4, 6 or portions thereof as determined using the Bestfit procedure of the DNA sequence analysis software package developed by the Genetic Computer Group (GCG) at the university of Wisconsin (gap creation penalty −50, gap extension penalty −3).

According to still another aspect of the present invention there is provided an isolated nucleic acid comprising a polynucleotide encoding a polypeptide being at least 60%, preferably at least 65%, more preferably at least 70%, still preferably at least 75%, yet preferably at least 80%, more preferably at least 85%, more preferably at least 90%, most preferably at least 95%–100%, homologous with SEQ ID NOs:3, 5, 7 or portions thereof as determined using the Bestfit procedure of the DNA sequence analysis software package developed by the Genetic Computer Group (GCG) at the university of Wisconsin (gap creation penalty −50, gap extension penalty −3).

As used herein in the specification and in the claims section that follows, the term "homologous" refers to identical+similar.

According to an additional aspect of the present invention there is provided a recombinant protein comprising a polypeptide encoded by the polynucleotides herein described.

The necleic acid according to the present invention can be a complementary polynucleotide sequence, genomic polynucleotide sequence or a composite polynucleotide sequence.

As used herein the phrase "complementary polynucleotide sequence" includes sequences which originally result from reverse transcription of messenger RNA using a reverse transcriptase or any other RNA dependent DNA polymerase. Such sequences can be subsequently amplified in vivo or in vitro using a DNA dependent DNA polymerase.

As used herein the phrase "genomic polynucleotide sequence" includes sequences which originally derive from a chromosome and reflect a contiguous portion of a chromosome.

As used herein the phrase "composite polynucleotide sequence" includes sequences which are at least partially complementary and at least partially genomic. A composite sequence can include some exonal sequences required to encode a polypeptide, as well as some intronic sequences interposing therebetween. The intronic sequences can be of any source, including of other genes, and typically will include conserved splicing signal sequences. Such intronic sequences may further include cis acting expression regulatory elements.

Thus, this aspect of the present invention encompasses (i) polynucleotides as set forth in SEQ ID NOs:1, 4 and 6; (ii) fragments or portions thereof; (iii) sequences hybridizable therewith; (iv) sequences homologous thereto; (v) genomic and composite sequences coresponding thereto; (vi) sequences encoding similar polypeptides with different codon usage; and (vii) altered sequences characterized by mutations, such as deletion, insertion or substitution of one or more nucleotides, either naturally occurring or man induced, either randomly or in a targeted fashion.

According to yet an additional aspect of the present invention there is provided a recombinant protein comprising a polypeptide at least 60%, preferably at least 65%, more preferably at least 70%, still preferably at least 75%, yet preferably at least 80%, more preferably at least 85%, more preferably at least 90%, most preferably at least 95%–100%, homologous with SEQ ID NOs:3, 5, 7 or portions thereof, as determined using the Bestfit procedure of the DNA sequence analysis software package developed by the Genetic Computer Group (GCG) at the university of Wisconsin (gap creation penalty −50, gap extension penalty −3).

According to still an additional aspect of the present invention there is provided a nucleic acid construct comprising the isolated nucleic acid herein described.

According to a preferred embodiment of the present invention the nucleic acid construct further comprising a promoter for regulating the expression of the isolated nucleic acid in a sense or antisense orientation. Such promoters are known to be cis-acting sequence elements required for transcription as they serve to bind DNA dependent RNA polymerase which transcribes sequences present downstream thereof. Such down stream sequences can be in either one of two possible orientations to result in the transcription of sense RNA which is translatable by the ribozyme machinery or antisense RNA which typically does not contain translatable sequences, yet can duplex or triplex with endogenous sequences, either mRNA or chromosomal DNA and hamper gene expression, all as further detailed hereinunder.

While the isolated nucleic acid described herein is an essential element of the invention, it is modular and can be used in different contexts. The promoter of choice that is used in conjunction with this invention is of secondary importance, and will comprise any suitable promoter. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest. These elements may be selected from transcriptional regulators that activate the transcription of genes essential for the survival of these cells in conditions of stress or starvation, including, but not limited to, the heat shock proteins.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in E. coli (wherein the construct comprises an appropriate selectable marker and origin of replication) and be compatible for propagation in cells, or integration in the genome, of an organism of choice. The construct according to this aspect of the present invention can be for example, a plasmid, a bacmid, a phagemid, a cosmid, a phage, a virus or an artificial chromosome.

Alternatively, the nucleic acid construct according to this aspect of the present invention further includes a positive and a negative selection markers and may therefore be employed for selecting for homologous recombination events, including, but not limited to, homologous recombination employed in knock-in and knock-out procedures. One ordinarily skilled in the art can readily design a knock-out or knock-in constructs including both positive and negative selection genes for efficiently selecting transfected embryonic stem cells that underwent a homologous recombination event with the construct. Such cells can be introduced into developing embryos to generate chimeras, the offspring thereof can be tested for carrying the knock-out or knock-in constructs. Knock-out and/or knock-in constructs according to the present invention can be used to further investigate the functionality of the new gene. Such constructs can also be used in somatic and/or germ cells gene therapy to destroy activity of a defective, gain of function allele or to replace the lack of activity of a silent allele in an organism, thereby to down or upregulate activity, as required. Further detail relating to the construction and use of knock-out and knock-in constructs can be found in Fukushige, S. and Ikeda, J. E.: Trapping of mammalian promoters by Cre-lox site-specific recombination. DNA Res 3 (1996) 73–80; Bedell, M. A., Jenkins, N. A. and Copeland, N. G.: Mouse models of human disease. Part I: Techniques and resources for genetic analysis in mice. Genes and Development 11 (1997) 1-11; Beringham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751–62, which are incorporated herein by reference.

According to yet another aspect of the present invention there is provided a host cell or animal comprising a nucleic acid construct or a portion thereof as described herein. Methods of transforming host cells, both prokaryotes and eukaryotes, and organisms with nucleic acid constructs and selection of transformants (e.g., transformed cells or transgenic animals) are well known to those of skills in the art. In addition, once transfected, such cells and organisms can be designed to direct the production of ample amounts of a recombinant protein which can then be purfied by known methods, including, but not limited to, various chromatography and gel electrophoresis methods. Such a purified recombinant protein can serve for elicitation of antibodies as further detailed hereinunder. Methods of transformation of cells and organism are described in detail in reference 43, whereas methods of recombinant protein purification are described in detail in reference 52, both are incorporated herein by reference.

According to still another aspect of the present invention there is provided an oligonucleotide of at least 17, at least 18, at least 19, at least 20, at least 22, at least 25, at least 30 or at least 40, bases specifically hybridizable with the isolated nucleic acid described herein.

Hybridization of shorter nucleic acids (below 200 bp in length, e.g. 17–40 bp in length) is effected by stringent, moderate or mild hybridization, wherein stringent hybridization is effected by a hybridization solution of 6×SSC and 1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 1–1.5° C. below the $T_m$, final wash solution of 3 M TMACl, 0.01 M sodium phosphate (pH 6.8), 1 mM EDTA (pH 7.6), 0.5% SDS at 1–1.5° C. below the $T_m$; moderate hybridization is effected by a hybridization solution of 6×SSC and 0.1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 2–2.5° C. below the $T_m$, final wash solution of 3 M TMACl, 0.01 M sodium phosphate (pH 6.8), 1 mM EDTA (pH 7.6), 0.5% SDS at 1–1.5° C. below the $T_m$, final wash solution of 6×SSC, and final wash at 22° C.; whereas mild hybridization is effected by a hybridization solution of 6×SSC and 1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 37° C., final wash solution of 6×SSC and final wash at 22° C.

According to an additional aspect of the present invention there is provided a pair of oligonucleotides each independently of at least 17, at least 18, at least 19, at least 20, at least 22, at least 25, at least 30 or at least 40 bases specifically hybridizable with the isolated nucleic acid described herein in an opposite orientation so as to direct exponential amplification of a portion thereof in a nucleic acid amplification reaction, such as a polymerase chain reaction. The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and zero ° C. Consequently, according to yet an additional aspect of the present invention there is provided a nucleic acid amplification product obtained using the pair of primers described herein. Such a nucleic acid amplification product can be isolated by gel electrophoresis or any other size based separation technique. Alternatively, such a nucleic acid amplification product can be isolated by affinity separation, either strandness affinity or sequence affinity. In addition, once isolated, such a product can be further genetically manipulated by restriction, ligation and the like, to serve any one of a plurality of applications associated with up and/or down regulation of activity.

According to still an additional aspect of the present invention there is provided an antisense oligonucleotide comprising a polynucleotide or a polynucleotide analog of at least 10 bases, preferably between 10 and 15, more preferably between 50 and 20 bases, most preferably, at least 17, at least 18, at least 19, at least 20, at least 22, at least 25, at least 30 or at least 40 bases being hybridizable in vivo, under physiological conditions, with (i) a portion of a polynucleotide strand encoding a polypeptide at least 60%, preferably at least 65%, more preferably at least 70%, still preferably at least 75%, yet preferably at least 80%, more preferably at least 85%, more preferably at least 90%, most preferably at least 95%–100% homologous to SEQ ID NOs:3, 5, 7 or portions thereof as determined using the as determined using the Bestfit procedure of the DNA sequence analysis software package developed by the Genetic Computer Group (GCG) at the university of Wisconsin (gap creation penalty –50, gap extension penalty –3); or (ii) a portion of a polynucleotide strand at least 60%, preferably at least 65%, more preferably at least 70%, still preferably at least 75%, yet preferably at least 80%, more preferably at least 85%, more preferably at least 90%, most preferably at least 95%–100% identical with SEQ ID NOs:1, 4, 6 or portions thereof as determined using the Bestfit procedure of the DNA sequence analysis software package developed by the Genetic Computer Group (GCG) at the university of Wisconsin (gap creation penalty –12, gap extension penalty –4).

Such antisense oligonucleotides can be used to downregulate gene expression as further detailed hereinunder. Such an antisense oligonucleotide is readily synthesizable using solid phase oligonucleotide synthesis.

The ability of chemically synthesizing oligonucleotides and analogs thereof having a selected predetermined sequence offers means for down modulating gene expression. Three types of gene expression modulation strategies may be considered.

At the transcription level, antisense or sense oligonucleotides or analogs that bind to the genomic DNA by strand displacement or the formation of a triple helix, may prevent transcription. At the transcript level, antisense oligonucleotides or analogs that bind target mRNA molecules lead to the enzymatic cleavage of the hybrid by intracellular RNase H. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. As a result, in both cases, the number of the target mRNA intact transcripts ready for translation is reduced or eliminated. At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs.

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool.

For example, several antisense oligonucleotides have been shown to arrest hematopoietic cell proliferation, growth, entry into the S phase of the cell cycle, reduced survival and prevent receptor mediated responses.

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are typically impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters.

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, α-anomeric bridges and borane derivatives.

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—$SO_2$—).

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal region and may be pegylated.

Thus, antisense technology requires pairing of messenger RNA with an oligonucleotide to form a double helix that inhibits translation. The concept of antisense-mediated gene therapy was already introduced in 1978 for cancer therapy. This approach was based on certain genes that are crucial in cell division and growth of cancer cells. Synthetic fragments of genetic substance DNA can achieve this goal. Such molecules bind to the targeted gene molecules in RNA of tumor cells, thereby inhibiting the translation of the genes and resulting in dysfunctional growth of these cells. Other mechanisms has also been proposed. These strategies have been used, with some success in treatment of cancers, as well as other illnesses, including viral and other infectious diseases. Antisense oligonucleotides are typically synthesized in lengths of 13–30 nucleotides. The life span of oligonucleotide molecules in blood is rather short. Thus, they have to be chemically modified to prevent destruction by ubiquitous nucleases present in the body. Phosphorothioates are very widely used modification in antisense oligonucleotide ongoing clinical trials. A new generation of antisense molecules consist of hybrid antisense oligonucleotide with a central portion of synthetic DNA while four bases on each end have been modified with 2'O-methyl ribose to resemble RNA. In preclinical studies in laboratory animals, such compounds have demonstrated greater stability to metabolism in body tissues and an improved safety profile when compared with the first-generation unmodified phosphorothioate. Dosens of other nucleotide analogs have also been tested in antisense technology.

RNA oligonucleotides may also be used for antisense inhibition as they form a stable RNA—RNA duplex with the target, suggesting efficient inhibition. However, due to their low stability RNA oligonucleotides are typically expressed inside the cells using vectors designed for this purpose. This approach is favored when attempting to target a mRNA that encodes an abundant and long-lived protein.

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively, they may prevent duplex unwinding and, therefore, transcription of genes within the triple helical structure.

Thus, according to a further aspect of the present invention there is provided a pharmaceutical composition comprising the antisense oligonucleotide described herein and a pharmaceutically acceptable carrier. The pharmaceutically acceptable carrier can be, for example, a liposome loaded with the antisense oligonucleotide. Formulations for topical administration may include, but are not limited to, lotions, ointments, gels, creams, suppositories, drops, liquids, sprays and powders. Conventional pharmaceutical carriers, aqueous, powder or oily bases, thickeners and the like may be necessary or desirable. Compositions for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include, but are not limited to, sterile aqueous solutions which may also contain buffers, diluents and other suitable additives.

According to still a further aspect of the present invention there is provided a ribozyme comprising the antisense oligonucleotide described herein and a ribozyme sequence fused thereto. Such a ribozyme is readily synthesizable using solid phase oligonucleotide synthesis.

Riboymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

According to still another aspect of the present invention there is provided an antibody comprising an immunoglobulin specifically recognizing and binding a polypeptide at least 60%, preferably at least 65%, more preferably at least 70%, still preferably at least 75%, yet preferably at least 80%, more preferably at least 85%, more preferably at least 90%, most preferably at least 95%–100% homologous (identical+similar) to SEQ ID NOs:3, 5, 7 or portions thereof using as determined using the Bestfit procedure of the DNA sequence analysis software package developed by the Genetic Computer Group (GCG) at the university of Wisconsin (gap creation penalty –50, gap extension penalty –3). According to a preferred embodiment of this aspect of the present invention the antibody specifically recognizing and binding the polypeptides set forth in SEQ ID NOs:3, 5, 7 or portions thereof.

The present invention can utilize serum immunoglobulins, polyclonal antibodies or fragments thereof, (i.e., immunoreactive derivative of an antibody), or monoclonal antibodies or fragments thereof. Monoclonal antibodies or purified fragments of the Monoclonal antibodies having at least a portion of an antigen binding region, including such as Fv, F(ab1)$_2$, Fab fragments (Harlow and Lane, 1988 Antibody, Cold Spring Harbor), single chain antibodies (U.S. Pat. No. 4,946,778), chimeric or humanized antibodies and complementarily determining regions (CDR) may be prepared by conventional procedures. Purification of these serum immunoglobulins antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104–126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes includes IgD, IgE, IgA, IgM and related proteins.

Methods for the generation and selection of monoclonal antibodies are well known in the art, as summarized for example in reviews such as Tramontano and Schloeder, Methods in Enzymology 178, 551–568, 1989. A recombinant protein of the present invention may be used to generate antibodies in vitro. More preferably, the recombinant protein of the present invention is used to elicit antibodies in vivo. In general, a suitable host animal is immunized with the recombinant protein of the present invention. Advantageously, the animal host used is a mouse of an inbred strain. Animals are typically immunized with a mixture comprising a solution of the recombinant protein of the present invention in a physiologically acceptable vehicle, and any suitable adjuvant, which achieves an enhanced immune response to the immunogen. By way of example, the primary immunization conveniently may be accomplished with a mixture of a solution of the recombinant protein of the present invention and Freund's complete adjuvant, said mixture being prepared in the form of a water in oil emulsion. Typically the immunization may be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the recombinant protein can be determined during the immunization schedule by any convenient method including by way of example radioimmunoassay, or enzyme linked immunosorbant assay, which is known as the ELISA assay. When suitable antibody titers are achieved, antibody producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multiwell plates, and the culture supernatants are screened to identify cultures containing antibodies that recognize the hapten of choice. Hybridomas that secrete antibodies that recognize the recombinant protein of the present invention are cloned by limiting dilution and expanded, under appropriate culture conditions. Monoclonal antibodies are purified and characterized in terms of immunoglobulin type and binding affinity.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., molecular Cloning—A Laboratory Manual, Cold Spring Harbor Laboratory, Cold Spring Harbor, N.Y. (1989), which is incorporated herein by reference. Other general references are provided throughout this document The procedures therein are believed to be well known in the art and are provided for the convenience of the reader. All the information contained therein is incorporated herein by reference.

Materials and Experimental Methods

The following protocols and experimental details are referenced in the Examples that follow:

RT-PCR:

RNA was prepared using TRI-Reagent (Molecular research center Inc.) according to the manufacturer instructions. 1.25 µg were taken for reverse transcription reaction using SuperScriptII Reverse transcriptase (Gibco BRL) and Oligo $(dT)_{15}$ primer (SEQ ID NO:22), (Promega). Amplification of the resultant first strand cDNA was performed with Taq polymerase (Promega) or with Expand high fidelity (Boehringer Mannheim).

cDNA Sequence Analysis:

Sequence determinations were performed with vector specific and gene specific primers, using an automated DNA sequencer (Applied Biosystems, model 373A). Each nucleotide was read from at least two independent primers. Computation and sequence analysis and alignments were done using the DNA sequence analysis software package developed by the Genetic Computer Group (GCG) at the university of Wisconsin. Alignments of two sequences were performed using Bestfit (gap creation penalty −12, gap extension penalty −4) or with Gap program (gap creation penalty −50, gap extension penalty −3).

Tissue Distribution:

Tissue distribution of the hnhp1 transcript was determined by semi-quantitative PCR. cDNA panels were obtained from Clontech. PCR was performed with the gene specific primers hn1u350 (SEQ ID NO:12) and hn1l116 (SEQ ID NO:10). PCR program was as follows: 94° C., 3 minutes, followed by 40 cycles of 94° C., 45 seconds, 64° C., 1 minute, 72° C., 1 minute. Samples were taken for further analysis following 25, 30, 35 and 40 cycles.

Chromosome Localization:

Chromosome localization of hnhp1 was performed using the radiation hybrid panel Stanford G3. This panel was provided by the human genome center at the Weizmann Institute. A 225 bp genomic fragment of hnhp1 gene was

```
                  Primers list:

hn1l116    5'-GGAGAGCAAGTCTGTGTTGATTC-3'           (SEQ ID NO:10)
hn1l230    5'-CACTGGTAGCCATGAGTGTGAG-3'            (SEQ ID NO:11)
hn1u350    5'-TTGGTCATCCCTCCAGTCACCA-3'            (SEQ ID NO:12)
pn9-312u   5'-CTTGCCTGTAGACAGAGCTGCAG-3'           (SEQ ID NO:14)
hpu-685    5'-GAGCAGCCAGGTGAGCCCAAGA-3'            (SEQ ID NO:16)
hp1967     5'-TCAGATGCAAGCAGCAACTTTGGC-3'          (SEQ ID NO:17)
mn1u118    5'-CACCCTGATGTCATGCTGGAG-3'             (SEQ ID NO:18)
mn1l563    5'-CATCTAGGAGAGCAATGACGTTC-3'           (SEQ ID NO:19)
Ap1        5'-CCATCCTAATACGACTCACTATAGGGC-3'       (SEQ ID NO:20)
Ap2        5'-ACTCACTATAGGGCTCGAGCGGC-3'           (SEQ ID NO:21)
```

Southern Analysis:

Genomic DNA was extracted from animal or from human blood using Blood and cell culture DNA maxi kit (Qiagene). DNA was digested with EcoRI, separated by gel electrophoresis and transferred to a nylon membrane Hybond N+ (Amersham). PCR products underwent a similar procedure. Hybridization was performed at 68° C. in 6×SSC, 1% SDS, 5× Denharts, 10% dextran sulfate, 100 µg/ml salmon sperm DNA, and $^{32}p$ labeled probe. Pn9, a 1.7 kb fragment, which contain the entire open reading frame except for a deletion of 162 nucleotides (del:473–634, SEQ ID NO:1) was used as a probe. Following hybridization, the membrane was washed with 3×SSC, 0.1% SDS, at 68° C. and exposed to X-ray film for 3 days. Membranes were then washed with 0.1×SSC, 0.1% SDS, at 68° C. and were re-exposed for 4 days.

amplified using the gene specific primers hn1u350 (SEQ ID NO:12) and hn1l116 (SEQ ID NO:10). PCR program was as follows: 94° C., 3 minutes, followed by 39 cycles of 94° C. 45 seconds, 64° C., 1 minute, 72° C., 1 min. Analysis of results was done through the RH server at the Stanford human genome center.

Example 1

Cloning an EST for a Novel Heparanase Gene

The entire amino acid sequence of human heparanase (SEQ ID NO:9) was used to screen human EST database for homologous sequences. Screening was performed using the BLAST 2.0 server at the NCBI, basic BLAST search, tblastn program.

A distantly homologous fragment was pooled out, accession number AI222323, IMAGE clone number 1843155 from Soares_NFL_T_GBC_S1 *Homo Sapiens* cDNA library prepared from testis B-cells and fetal lungs. The search values for this sequence were as follows: Score=38.3 bits (87), Expect=0.15 Identities=16/36 (44%), Positives=22/36 (60%). The sequence of accession number AI222323 contains 378 nucleotides of the 3' of clone 1843155 (complementary to nucleotides 165–543 of SEQ ID NO:23).

This clone was purchased from the IMAGE consortium. It contained an insert of 560 bp (SEQ ID NO:23). The entire nucleotide sequence was determined and compared to the hpa cDNA encoding human heparanase. The homology between clone 1843155 and hpa cDNA was restricted to the 3' region of the cDNA clone. There was 59% homology between nucleotides 99–275 of clone 1843155 (SEQ ID NO:23), and 1532–1708 of hpa (SEQ ID NO:24). The deduced amino acid sequence of this region, had 60% homology (identical+similar) to amino acids 488–542 (SEQ ID NO:9) of human heparanase. The downstream sequence (nucleotides 276–560, SEQ ID NO:23) represents a 3' untranslated region and a poly A tail. The upstream sequence, nucleotides 1–98 (SEQ ID NO:23) was unrelated to heparanase. This unrelated sequence was found to be identical to a different cDNA clone from the same library. Therefore, the human EST clone 1843155, obtained from the IMAGE consortium is assumed to be a chimera, which contains two unrelated partial cDNAs ligated to a single vector.

Example 2

Cloning a cDNA for a Novel Heparanase Gene

In order to isolate the entire cDNA, three primers were designed according to the sequence of clone 1843155. The cDNA was amplified from placenta cDNA by Marathon RACE (rapid amplification of cDNA ends) (Clontech, Palo Alto, Calif.) according to the manufacturer instructions. The first cycle was performed with the gene specific primer hn11116 (SEQ ID NO:10) and the universal primer Ap1 (SEQ ID NO:20). The second cycle was performed with the gene specific primer hn11230 (SEQ ID NO:11) and the universal primer Ap2 (SEQ ID NO:21). Following amplification, a difused band of approximately 1.7 kb was obtained. This cDNA amplification product was subcloned into pGEM T-easy (Promega, Madison, Wis.) and the nucleotide sequences of three independent clones pn5, pn6 and pn9 were determined. The consensus sequence of the longest cDNA, pn6, appears in FIG. 1 (SEQ ID NOs:1, 2 and 3). It is 2060 nucleotide long and it contains an open reading frame of 1776 nucleotides, which encodes a polypeptide of 592 amino acids, with a calculated molecular weight of 66.5 kDa. The newly cloned gene was designated hnhp1. The two shorter forms, pn9 and pn5 and their deduced amino acid sequences are set forth in SEQ ID NOs:4 and 6 and SEQ ID NO:5 and 7, respectively. Pn9 and pn5 were identical to pn6, however each one of then contained an in frame deletion as a result of alternative splicing. Pn9 contains a deletion of 162 nucleotides, 473–634 of SEQ ID NO:1, which correspond to amino acids 150–203 of SEQ ID NO:3. As a result pn9 encodes a putative polypeptide of 538 amino acids (SEQ ID NO:5) having a calculated molecular weight of 60.4 kDa. Pn5 contains a deletion of 336 nucleotides, 473–808 of SEQ ID NO:1, which correspond to amino acids 150–261 of SEQ ID NO:3, thus, it encodes a putative polypeptides of 480 amino acids (SEQ ID NO:7) having a calculated molecular weight of 53.9 kDa. The $11^{th}$ amino acid residue of SEQ ID NO:3 is methionine. It is generally accepted that the first methionine serves as a translation start site in mammals, however, the nucleotides surrounding the second ATG fit better with the Kozak consensus sequence for translation start site. Translation may thus start at the second methionine and produce a protein of 581 amino acids with calculated molecular weight of 65.4 kDa. The presence of transcripts of variable length was confirmed by PCR amplification of the hn1hp cDNA using two gene specific primers: pn9-312u (SEQ ID NO:14) which is located close to the 5' end and hn11230 (SEQ ID NO:111) which overlaps the stop codon at the 3' end of the open reading frame. Amplification was performed from Marathon ready cDNA prepared from placenta and from testis. The PCR products are shown in FIG. 3. Four bands were obtained from placenta: two major bands of 1.45 and 1.6 kb, similar to pn9 and pn6 and two minor bands, one of 1.35 kb, similar to pn5 and a second one of 1.8 kb. The sequence of the latter has not yet been determined. Amplification of testis cDNA resulted in a different pattern. Four bands of 1.35, 1.65, 1.85 and 2.05 kb were observed and a minor one of 1.5 kb. The various forms appear to represent products of alternative splicing. Since the deletions characterized so far retain an open reading frame, the translation products of the various cDNAs may constitute a protein family. The comparison between the amino acid sequence of hnhp1 and heparanase is shown in FIG. 3. Using the gap program of the GCG package which aligns the entire amino acid sequences, the homology between the two proteins is 45.5% identity and 7.3% similarity, total homology of 52.8% (gap creation penalty −50, gap extension penalty −3). The BestFit program defines the region of the best homology between the two sequences. Using this program, the homology between the two amino acid sequences starts at position 63 of hn1hp1 (SEQ ID NO:3) and position 41 of heparanase (SEQ ID NO:9) and is 47.5% identity and 7.8% similarity, i.e. homology of 55.3%. The homology between the nucleotide sequences of hnhp1 and hpa is 57% as calculated by the BestFit program. The homologous region is located between nucleotides 638–1812 of hnhp1 (SEQ ID NO: 1) and nucleotides 564–1708 of hpa (SEQ ID NO:24). Using the Gap program the homology is 51% over the entire sequence gap creation penalty −50, gap extension penalty −3.

Example 3

Zoo Blot

Hnhp1 cDNA was used as a probe to detect homologous sequences in human DNA and in DNA of various animals. The autoradiogram of the Southern analysis is presented in FIG. 4. Several bands were detected in human DNA. Several intense bands were detected in all mammals, while faint bands were detected in chicken. This correlates with the phylogenetic relation between human and the tested animals. The intense bands indicate that hnhp1 is conserved among mammals as well as in more genetically distant organisms. The multiple bands patterns suggest that in all animals, hnhp1 locus occupies a large genomic region. Several specific bands disappeared after stringent wash. These may represent homologous sequences and suggest the existence of a gene family, which can be isolated based on their homology to the human hnhp1 reported here.

Example 4

Comparison to Heparanase via Cross Hybridization

In order to check the capability of hpa and hnhp1 to cross hybridize under low stringency conditions, the entire coding region of the human hpa and hnhp1 were amplified by PCR.

Figure 4:
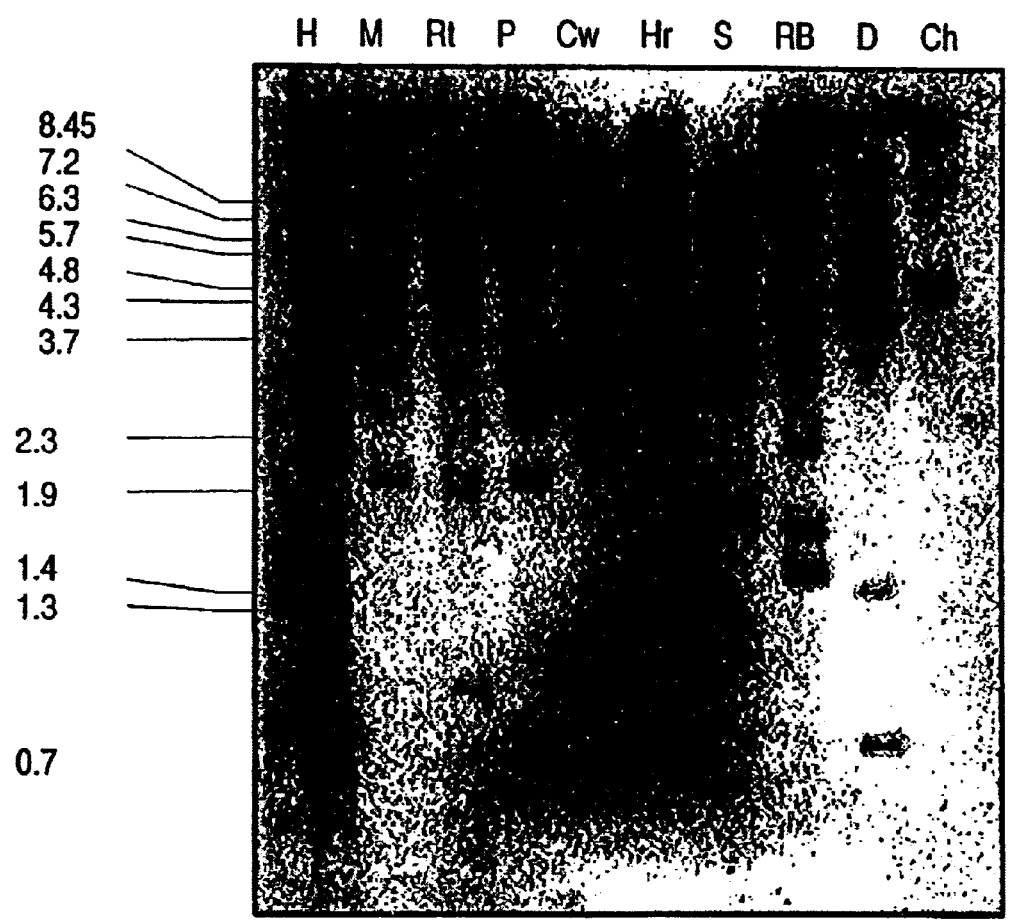
FIG. 4 shows a zoo blot. Ten micrograms of genomic DNA from various species were digested with EcoRI and separated on 0.7% agarose-TBE gel. Following electrophoresis, the gel was treated with HCl and then with NaOH and the DNA fragments were downward transferred to a nylon membrane (Hybond N+, Amersham) with 0.4 N NaOH. The membrane was hybridized with a 1.7 Kb DNA probe that contained the hnhp1 cDNA (clone pn9). Lane order: H—Human; M—Mouse; Rt—Rat; P—Pig; Cw—Cow; Hr—Horse; S—Sheep; Rb—Rabbit; D—Dog; Ch—Chicken; F—Fish. Size markers (Lambda BsteII) are shown on the left.

Human hpa was amplified from platelets mRNA by RT-PCR using the primers hpu-685 (SEQ ID NO:16) and hp1967 (SEQ ID NO:17), and hnhp1 was amplified from testis using the primers hn1230 (SEQ ID NO:11) and pn9-312u (SEQ ID NO:14). The products were quantified and samples of 100 pg and 1 ng were run on agarose gel and subjected to Southern hybridization. The membranes were probed with $^{32}$p labeled hpa cDNA and with hnhp1 cDNA. No cross hybridization was observed (FIG. 5) even after over exposure for 5 days. Since hpa is the most similar sequence known today to that of hnhp1, this experiment indicates that the bands detected in the autoradiograph of FIG. 4 are of the hnhp1 gene or of yet unknown sequences homologous thereto, which might constitute a gene family. This further indicated that such sequences are isolatable using the hnhp1 as a probe to screen the relevant libraries, or using hnhp1 derived PCR primers to amplify the relevant cDNA or DNA sequences.

Example 5

Chromosome Localization

The chromosome localization of hnhp1 was determined using G3 radiation hybrid panel. Hnhp1 was amplified from 83 human/mouse radiation hybrids. The results were analyzed by the RH server and the hnhp1 gene was mapped to chromosome 10, next to the marker SHGC-57721. The results also indicated a possibility of a second copy of the gene.

Example 6

Expression Pattern of hnhp1

The tissue distribution of hnhp1 transcripts was determined using calibrated human cDNA panels (Clontech, Palo Alto, Calif.). The results are shown in Table 1 below. Expression level is generally low. PCR products were clearly observed only after 40 cycles of amplification.

TABLE 1

| Tissue | hn1 (40 cycles) |
| --- | --- |
| Bone marrow | |
| Liver | |
| Lymph node | + |
| Leukocytes | |
| Spleen | + |
| Thymus | |
| Tonsil | |
| Colon | + |
| Ovary | + |
| Prostate | ++ |
| Small intestine | ++ |
| Testis | +++ |

Example 7

Cloning of a Mouse Homologue

Screening of the mouse EST database with the amino acid sequence of heparanase as well as of hnhp1 pooled out a mouse EST clone, which shares distant homology with heparanase and a remarkably high homology with hnhp1. The EST clone 1378452 accession number AI019269 from mouse thymus was 351 nucleotide long and it is set forth in SEQ ID NO:8. It has 61–63% identity over 161 nucleotides (191–351, SEQ ID NO:8) to the human (SEQ ID NO:24) and mouse (SEQ ID NO:15) hpa nucleotide sequences, and 93% to hnhp1 nucleotide sequence (SEQ ID NO:1) using the BestFit program of the GCG package. The nucleotide sequence of this clone did not contain an open reading frame. Two frame shifts were identified in the sequence found in the EST database, as compared to the hnhp1 sequence. This frame shifts were later confirmed by nucleotide sequence analysis of this clone as well as by isolation of this fragment from BL6 mouse melanoma cells and determination of its nucleotide sequence. This mouse gene is transcribed at very low levels. Low levels of expression were indicated as no amplification products were obtained following 40 cycles of PCR from mouse cDNA panel (Clontech, Palo Alto, Calif.) which included cDNA from mouse heart, brain, spleen, lung, liver, skeletal muscle, kidney, testis and embryos of 7, 11, 15, and 17 days. The amplification was performed using the gene specific primers mn1u118 (SEQ ID NO:18) and mn11563 (SEQ ID NO:19).

Example 8

Expression of hnhp1 in Mammalian Cells

A mammalian expression vector was constructed in order to over-express hnhp1 in human cells. To enable detection of the Hnhp1 translation product, the hnhp1 expression vector was designed to encode a C-terminal tagged hn1 protein. A DNA sequence, which encodes eight amino acids FLAG (Kodak), was fused to the 3' end of the hnhp1 open reading frame.

Fusion of the FLAG sequence to the hnhp1 coding sequence was generated by PCR amplification using the primer: hn1-c-flag: 5'-A-3' (SEQ ID NO:25) and the primer: pn9-312u (SEQ ID NO:14). The PCR program was as follows: 94° C., 3 min followed by 5 cycles of: 94° C., 45 seconds, 50° C., 45 seconds and 72° C., 2 minutes, and then 32 cycles of 94° C., 45 seconds, 64° C., 45 seconds and 72° C., 2 min.

The amplification product was subcloned into pGEM-T-easy, and the sequence was verified. The resulting plasmids were designated pGEM-pn6F and pGEM-pn9F.

Two constructs were generated in pSI mammalian expression vector (Promega): the first contained the complete hnhp1 sequence (pn6) and the second contained the alternative splice form (pn9). The pSI-pn6 expression vector was constructed by triple ligation of the following fragments: an EcoRI-BamHI fragment, which contains the 5' end of hn1-pn6, excised from pGem-T-easy-pn9, a BamHI-NotI fragment which contains the 3'FLAG tagged hnhp1, excised from pGEM-pn6F and pSI digested with EcoRI-NotI.

The pSI-pn9 expression vector was constructed similarly, by triple ligation of the following fragments: an EcoRI-SspI fragment, which contains the 5' end of hnhp1-pn6, excised from pGem-T-easy-pn9, an SspI-NotI fragment, which contains the 3'FLAG tagged hnhp1, excised from pGem-pn6F and pSI digested with EcoRI-NotI.

The resulting plasmids were transfected into human embryonal kidney 293 cells, using the Fugene transfection reagent (Boehringer Mannheim). Forty-eight hours following transfection cells were harvested and proteins were analysed by western blot. Cell lysates of $2.5 \times 10^5$ were separated by SDS-PAGE, transferred onto a nylon membrane and incubated with anti FLAG antibody 1:1000 dilution (Kodak anti FLAG M2 cat: IB13025, final concentration 10 μg/ml). Proteins of approximately 65 kDa and 60 kDa were detected in cells transfected with pSI-pn6F and pSI-pn9F respectively. These proteins are similar in size to those predicted by the calculated molecular weight for the translation products of corresponding open reading frames. It is demonstrated that both the entire hnhp1 cDNA and the pn9 splice form are successfully transcribed and translated in human 293 cells. However, unlike heparanase the Hnhp1 protein products do not undergo major processing in these cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

LIST OF REFERENCES

1. Durand, P., Lehn, P., Callebaut, I., Fabrega, S., Henrissat, B. and Mornon, J. P. (1997). Active-site motifs of lysosomal acid hydrolases: invariant features of clan GH-A glycosyl hydrolases deduced from hydrophobic cluster analysis. Glycobiology, 7(2), 277–284.
2. Vlodavsky, I., Friedmann, Y., Elkin, M., Aingorn, H., Atzmon, R., Ishai-Michaeli, R., Bitan, M., Pappo, O., Peretz, T., Michal, I., Spector, L. and Pecker I. (1999). Mammalian heparanase: gene cloning, expression and function in tumor progression and metastasis. Nature Medicine (In press)
3. Wight, T. N., Kinsella, M. G., and Qwarnstromn, E. E. (1992). The role of proteoglycans in cell adhesion, migration and proliferation. Curr. Opin. Cell Biol., 4, 793–801.
4. Jackson, R. L., Busch, S. J., and Cardin, A. L. (1991). Glycosaminoglycans: Molecular properties, protein interactions and role in physiological processes. Physiol. Rev., 71, 481–539.
5. Wight, T. N. (1989). Cell biology of arterial proteoglycans. Arteriosclerosis, 9, 1–20.
6. Kjellen, L., and Lindahl, U. (1991). Proteoglycans: structures and interactions. Annu. Rev. Biochem., 60, 443–475.
7. Ruoslahti, E., and Yamaguchi, Y. (1991). Proteoglycans as modulators of growth factor activities. Cell, 64, 867–869.
8. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fl.
9. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fl.
10. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127.
11. Nakajima, M., Irimura, T., and Nicolson, G. L. (1988). Heparanase and tumor metastasis. J. Cell. Biochem., 36, 157–167.
12. Vlodavsky, I. et al. Invasion Metastasis 1995, 14:290–302.
13. Nakagima, M. et al. J. Cell. Biochem. 1988, 36:157–167.
14. Vlodavsky, I. et al. Cancer res. 1983, 43:2704–2711.
15. Vlodavsky, I. et al. J. Med 1988, 24:464–470.
16. Vlodavsky, I. et al. Invasion and Metastasis 12:112–127.
17. Gilat, D. et al. J. Exp. Med. 1995, 181:1929–1934.
18. Matzner et al. 1985, J. Clin. Invest. 10:1306–1313.
19. Mollinedo, F. et al. Biochem. J. 1997, 327:917–923.
20. Murphy, G. et al. Biochem. J. 1990, 192:517–525.
21. Nakajima, M. et al. J. Cell. Biochem. 1988, 36(2):157–167.
22. Ishai-Michaeli R. wt al. Cell Reg. 1990, 1:833–842.
23. Cardon-Cardo C. et al. Lab. Inrest. 1990, 63:832–840.
24. Nicolson, G. L. (1988). Organ specificity of tumor metastasis: Role of preferential adhesion, invasion and growth of malignant cells at specific secondary sites. Cancer Met. Rev., 7, 143–188.
25. Liotta, L. A., Rao, C. N., and Barsky, S. H. (1983). Tumor invasion and the extracellular matrix. Lab. Invest., 49, 639–649.
26. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711.
27. Sun L, Feusi E, Sibalic A, Beck-Schimmer B, Wuthrich R P (1998). Expression profile of hyaluronidase mRNA transcripts in the kidney and in renal cells. Kidney Blood Press Res; 21(6):413–8
28. Parish, C. R, Coombe, D. R., Jakobsen, K. B., and Underwood, P. A. (1987). Evidence that sulphated polysaccharides inhibit tumor metastasis by blocking tumor cell-derived heparanase. Int. J. Cancer, 40, 511–517.
29. Burgess, W. H., and Maciag, T. (1989). The heparin-binding (fibroblast) growth factor family of proteins. Annu. Rev. Biochem., 58, 575–606.
30. Folkman, J., and Klagsbrun, M. (1987). Angiogenic factors. Science, 235, 442–447.
31. Vlodavsky, I., Folkman, J., Sullivan, R., Fridman, R. Ishai-Michaelli, R., Sasse, J., and Klagsbrun, M. (1987). Endothelial cell-derived basic fibroblast growth factor: Synthesis and deposition into subendothelial extracellular matrix. Proc. Natl. Acad. Sci. USA, 84, 2292–2296.
32. Folkman, J., Klagsbrun, M., Sasse, J., Wadzinski, M., Ingber, D., and Vlodavsky, I. (1980). A heparin-binding angiogenic protein—basic fibroblast growth factor—is stored within basement membrane. Am. J. Pathol., 130, 393–400.
33. Bashkin, P., Doctrow, S., Klagsbrun, M., Svahn, C. M., Folkman, J., and Vlodavsky, I. (1989). Basic fibroblast growth factor binds to subendothelial extracellular matrix and is released by heparitinase and heparin-like molecules. Biochemistry, 28, 1737–1743.
34. Ishai-Michaeli, R., Svahn, C. -M., Chajek-Shaul, T., Korner, G., Ekre, H. -P., and Vlodavsky, I. (1992). Importance of size and sulfation of heparin in release of basic fibroblast factor from the vascular endothelium and extracellular matrix. Biochemistry, 31, 2080–2088.
35. Ishai-Michaeli, R., Eldor, A., and Vlodavsky, I. (1990). Heparanase activity expressed by platelets, neutrophils and lymphoma cells releases active fibroblast growth factor from extracellular matrix. Cell Reg., 1, 833–842.
36. Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci., 16, 268–271.
37. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fl.

38. Yayon, A., Klagsbrun, M., Esko, J. D., Leder, P., and Ornitz, D. M. (1991). Cell surface, heparin-like molecules are required for binding of basic fibroblast growth factor to its high affinity receptor. Cell, 64, 841–848.
39. Spivak-Kroizman, T., Lemmon, M. A., Dikic, I., Ladbury, J. E., Pinchasi, D., Huang, J., Jaye, M., Crumley, G., Schlessinger, J., and Lax, I. (1994). Heparin-induced oligomerization of FGF molecules is responsible for FGF receptor dimerization, activation, and cell proliferation. Cell, 79, 1015–1024.
40. Ornitz, D. M., Herr, A. B., Nilsson, M., West, a, J., Svahn, C. -M., and Waksman, G. (1995). FGF binding and FGF receptor activation by synthetic heparan-derived di- and trisaccharides. Science, 268, 432–436.
41. Gitay-Goren, H., Soker, S., Vlodavsky, I., and Neufeld, G. (1992). Cell surface associated heparin-like molecules are required for the binding of vascular endothelial growth factor (VEGF) to its cell surface receptors. J. Biol. Chem., 267, 6093–6098.
42. Ernst S, Langer R, Cooney CL, Sasisekharan R. (1995). Enzymatic degradation of glycosaminoglycans. Crit Rev Biochem Mol Biol, 30(5):387–444.
43. Current protocols in molecular biology (1994–1999). Ausubel, F. M., Brent, R., Kingston, R. E., Moore D. D., Seidman, J. G., Smith, J. A., Struhl, K. Eds. JohnWiley & Sons, Inc.
44. Rapraeger, A., Krufka, A., and Olwin, B. R. (1991). Requirement of heparan sulfate for bFGF-mediated fibroblast growth and myoblast differentiation. Science, 252, 1705–1708.
45. Shieh, M -T., Wundunn, D., Montgomery, R. I., Esko, J. D., and Spear, P. G. J. (1992). Cell surface receptors for herpes simplex virus are heparan sulfate proteoglycans. J. Cell Biol., 116, 1273–1281.
46. Chen, Y., Maguire, T., Hileman, R. E., Fromm, J. R., Esko, J. D., Linhardt, R. J., and Marks, R. M. (1997). Dengue virus infectivity depends on envelope protein binding to target cell heparan sulfate. Nature Medicine 3, 866–871.
47. Putnak, J. R., Kanesa-Thasan, N., and Innis, B. L. (1997). A putative cellular receptor for dengue viruses. Nature Medicine 3, 828–829.
48. Narindrasorasak, S., Lowery, D., Gonzalez-DeWhitt, P., Poorman, R. A., Greenberg, B., Kisilevsky, R (1991). High affinity interactions between the Alzheimer's beta-amyloid precursor protein and the basement membrane form of theparan sulfate proteoglycan. J. Biol. Chem., 266, 12878–83.
49. Eisenberg, S., Sehayek, E., Olivecrona, T., and Vlodavsky, I. (1992). Lipoprotein lipase enhances binding of lipoproteins to heparan sulfate on cell surfaces and extracellular matrix. J. Clin. Invest., 90, 2013–2021.
50. Ross, R. (1993). The pathogenesis of atherosclerosis: a perspective for the 1990s. Nature (Lond.)., 362:801–809.
51. Zhong-Sheng, J., Walter, J., Brecht, R., Miranda, D., Mahmood Hussain, M., Innerarity, T. L. and Mahley, W. R. (1993). Role of heparan sulfate proteoglycans in the binding and uptake of apolipoprotein E-enriched remnant lipoproteins by cultured cells. J. Biol. Chem., 268, 10160–10167.
52. Current protocols in protein science (1996–1999). Coligan, J. E., Dunn, B. M., Ploegh, H. L., Speicher, D. W. and Wingfield, P. T. Eds. John Wiley & Sons Inc.

What is claimed is:

1. An isolated nucleic acid comprising SEQ ID No: 1, which sequence encodes a polypeptide comprising a conserved glycosyl hydrolase domain.

2. A nucleic acid construct comprising the isolated nucleic acid of claim 1.

3. A host cell comprising the nucleic acid construct of claim 2.

* * * * *

SEQUENCE LISTING

<160> NUMBER OF SEQ ID NOS: 25

<210> SEQ ID NO 1
<211> LENGTH: 2060
<212> TYPE: DNA
<213> ORGANISM: Homo sapiens

<400> SEQUENCE: 1

```
cgcttaattc tagaagaggg attgaatgag ggtgctttgt gccttccctg aagccatgcc      60
ctccagcaac tcccgccccc ccgcgtgcct agccccgggg gctctctact tggctctgtt     120
gctccatctc tcccttctcct cccaggctgg agacaggaga cccttgcctg tagacagagc    180
tgcaggtttg aaggaaaaga ccctgattct acttgatgtg agcaccaaga acccagtcag    240
gacagtcaat gagaacttcc tctctctgca gctggatccg tccatcattc atgatggctg    300
gctcgatttc ctaagctcca agcgcttggt gaccctggcc cggggacttt cgcccgcctt    360
tctgcgcttc gggggcaaaa ggaccgactt cctgcagttc cagaacctga ggaacccggc    420 gaaagccgc ggggccccgg gcccggatta ctatctcaaa aactatgagg atgacattgt    480
tcgaagtgat gttgccttag ataaacagaa aggctgcaag attgccagc accctgatgt    540 tatgctggag ctccaagggg agaaggcagc tcagatgcat ctggttcttc taaaggagca    600
attctccaat acttacagta atctcatatt aacagccagg tctctagaca aactttataa    660
ctttgctgat tgctctggac tccacctgat atttgctcta aatgcactgc gtcgtaatcc    720
caataactcc tggaacagtt ctagtgccct gagtctgttg aagtacagcg ccagcaaaaa    780
```

-continued

```
gtacaacatt tcttgggaac tgggtaatga gccaaataac tatcggacca tgcatggccg    840
ggcagtaaat ggcagccagt tgggaaagga ttacatccag ctgaagagcc tgttgcagcc    900
catccggatt tattccagag ccagcttata tggccctaat attgggcggc cgaggaagaa    960
tgtcatcgcc ctcctagatg gattcatgaa ggtggcagga agtacagtag atgcagttac   1020
ctggcaacat tgctacattg atggccgggt ggtcaaggtg atggacttcc tgaaaactcg   1080
cctgttagac acactctctg accagattag gaaaattcag aaagtggtta atacatacac   1140
tccaggaaag aagatttggc ttgaaggtgt ggtgaccacc tcagctggag cacaaacaa    1200 tctatccgat tcctatgctg caggattctt atggttgaac actttaggaa tgctggccaa   1260
tcagggcatt gatgtcgtga tacggcactc atttttttgac catggataca atcacctcgt   1320
ggaccagaat tttaacccat taccagacta ctggctctct ctcctctaca agcgcctgat   1380
cggccccaaa gtcttggctg tgcatgtggc tgggctccag cggaagccac ggcctggccg   1440
agtgatccgg gacaaactaa ggatttatgc tcactgcaca aaccaccaca accacaacta   1500
cgttcgtggg tccattacac ttttttatcat caacttgcat cgatcaagaa agaaaatcaa   1560
gctggctggg actctcagag acaagctggt tcaccagtac ctgctgcagc cctatgggca   1620
ggagggccta aagtccaagt cagtgcaact gaatggccag cccttagtga tggtggacga   1680
cgggaccctc ccagaattga agccccgccc ccttcgggcc ggccggacat tggtcatccc   1740
tccagtcacc atgggctttt tgtggtcaa gaatgtcaat gctttggcct ccgctaccg   1800 ataagctatc ctcacactca tggctaccag tgggcctgct gggctgcttc cactcctcca   1860
ctccagtagt atcctctgtt ttcagacatc ctagcaacca gcccctgctg ccccatcctg   1920
ctggaatcaa cacagacttg ctctccaaag agactaaatg tcatagcgtg atcttagcct   1980
aggtaggcca catccatccc aaaggaaaat gtagacatca cctgtaccta tataaggata   2040
aaggcatgtg tatagagcaa                                               2060
```

<210> SEQ ID NO 2
<211> LENGTH: 2060
<212> TYPE: DNA
<213> ORGANISM: Homo sapiens
<220> FEATURE:
<221> NAME/KEY: CDS
<222> LOCATION: (26)..(1801)

<400> SEQUENCE: 2

```
cgcttaattc tagaagaggg attga atg agg gtg ctt tgt gcc ttc cct gaa      52
                              Met Arg Val Leu Cys Ala Phe Pro Glu
                              1               5 gcc atg ccc tcc agc aac tcc cgc ccc ccc gcg tgc cta gcc ccg ggg     100
Ala Met Pro Ser Ser Asn Ser Arg Pro Pro Ala Cys Leu Ala Pro Gly
10              15                  20                  25 gct ctc tac ttg gct ctg ttg ctc cat ctc tcc ctt tcc tcc cag gct    148
Ala Leu Tyr Leu Ala Leu Leu Leu His Leu Ser Leu Ser Ser Gln Ala
                30                  35                  40 gga gac agg aga ccc ttg cct gta gac aga gct gca ggt ttg aag gaa    196
Gly Asp Arg Arg Pro Leu Pro Val Asp Arg Ala Ala Gly Leu Lys Glu
            45                  50                  55 aag acc ctg att cta ctt gat gtg agc acc aag aac cca gtc agg aca    244
Lys Thr Leu Ile Leu Leu Asp Val Ser Thr Lys Asn Pro Val Arg Thr
        60                  65                  70 gtc aat gag aac ttc ctc tct ctg cag ctg gat ccg tcc atc att cat    292
Val Asn Glu Asn Phe Leu Ser Leu Gln Leu Asp Pro Ser Ile Ile His
    75                  80                  85
```

-continued

```
gat ggc tgg ctc gat ttc cta agc tcc aag cgc ttg gtg acc ctg gcc      340
Asp Gly Trp Leu Asp Phe Leu Ser Ser Lys Arg Leu Val Thr Leu Ala
 90              95                 100                 105 cgg gga ctt tcg ccc gcc ttt ctg cgc ttc ggg ggc aaa agg acc gac      388
Arg Gly Leu Ser Pro Ala Phe Leu Arg Phe Gly Gly Lys Arg Thr Asp
                 110                 115                 120 ttc ctg cag ttc cag aac ctg agg aac ccg gcg aaa agc cgc ggg ggc      436
Phe Leu Gln Phe Gln Asn Leu Arg Asn Pro Ala Lys Ser Arg Gly Gly
             125                 130                 135 ccg ggc ccg gat tac tat ctc aaa aac tat gag gat gac att gtt cga      484
Pro Gly Pro Asp Tyr Tyr Leu Lys Asn Tyr Glu Asp Asp Ile Val Arg
         140                 145                 150 agt gat gtt gcc tta gat aaa cag aaa ggc tgc aag att gcc cag cac      532
Ser Asp Val Ala Leu Asp Lys Gln Lys Gly Cys Lys Ile Ala Gln His
155                 160                 165 cct gat gtt atg ctg gag ctc caa agg gag aag gca gct cag atg cat      580
Pro Asp Val Met Leu Glu Leu Gln Arg Glu Lys Ala Ala Gln Met His
170                 175                 180                 185 ctg gtt ctt cta aag gag caa ttc tcc aat act tac agt aat ctc ata      628
Leu Val Leu Leu Lys Glu Gln Phe Ser Asn Thr Tyr Ser Asn Leu Ile
                 190                 195                 200 tta aca gcc agg tct cta gac aaa ctt tat aac ttt gct gat tgc tct      676
Leu Thr Ala Arg Ser Leu Asp Lys Leu Tyr Asn Phe Ala Asp Cys Ser
             205                 210                 215 gga ctc cac ctg ata ttt gct cta aat gca ctg cgt cgt aat ccc aat      724
Gly Leu His Leu Ile Phe Ala Leu Asn Ala Leu Arg Arg Asn Pro Asn
         220                 225                 230 aac tcc tgg aac agt tct agt gcc ctg agt ctg ttg aag tac agc gcc      772
Asn Ser Trp Asn Ser Ser Ser Ala Leu Ser Leu Leu Lys Tyr Ser Ala
235                 240                 245 agc aaa aag tac aac att tct tgg gaa ctg ggt aat gag cca aat aac      820
Ser Lys Lys Tyr Asn Ile Ser Trp Glu Leu Gly Asn Glu Pro Asn Asn
250                 255                 260                 265 tat cgg acc atg cat ggc cgg gca gta aat ggc agc cag ttg gga aag      868
Tyr Arg Thr Met His Gly Arg Ala Val Asn Gly Ser Gln Leu Gly Lys
                 270                 275                 280 gat tac atc cag ctg aag agc ctg ttg cag ccc atc cgg att tat tcc      916
Asp Tyr Ile Gln Leu Lys Ser Leu Leu Gln Pro Ile Arg Ile Tyr Ser
             285                 290                 295 aga gcc agc tta tat ggc cct aat att ggg cgg ccg agg aag aat gtc      964
Arg Ala Ser Leu Tyr Gly Pro Asn Ile Gly Arg Pro Arg Lys Asn Val
         300                 305                 310 atc gcc ctc cta gat gga ttc atg aag gtg gca gga agt aca gta gat     1012
Ile Ala Leu Leu Asp Gly Phe Met Lys Val Ala Gly Ser Thr Val Asp
315                 320                 325 gca gtt acc tgg caa cat tgc tac att gat ggc cgg gtg gtc aag gtg     1060
Ala Val Thr Trp Gln His Cys Tyr Ile Asp Gly Arg Val Val Lys Val
330                 335                 340                 345 atg gac ttc ctg aaa act cgc ctg tta gac aca ctc tct gac cag att     1108
Met Asp Phe Leu Lys Thr Arg Leu Leu Asp Thr Leu Ser Asp Gln Ile
                 350                 355                 360 agg aaa att cag aaa gtg gtt aat aca tac act cca gga aag aag att     1156
Arg Lys Ile Gln Lys Val Val Asn Thr Tyr Thr Pro Gly Lys Lys Ile
             365                 370                 375 tgg ctt gaa ggt gtg gtg acc aca tca gct gga ggc aca aac aat cta     1204
Trp Leu Glu Gly Val Val Thr Thr Ser Ala Gly Gly Thr Asn Asn Leu
         380                 385                 390 tcc gat tcc tat gct gca gga ttc tta tgg ttg aac act tta gga atg     1252
Ser Asp Ser Tyr Ala Ala Gly Phe Leu Trp Leu Asn Thr Leu Gly Met
395                 400                 405
```

```
ctg gcc aat cag ggc att gat gtc gtg ata cgg cac tca ttt ttt gac    1300
Leu Ala Asn Gln Gly Ile Asp Val Val Ile Arg His Ser Phe Phe Asp
410                 415                 420                 425 cat gga tac aat cac ctc gtg gac cag aat ttt aac cca tta cca gac    1348
His Gly Tyr Asn His Leu Val Asp Gln Asn Phe Asn Pro Leu Pro Asp
                430                 435                 440 tac tgg ctc tct ctc ctc tac aag cgc ctg atc ggc ccc aaa gtc ttg    1396
Tyr Trp Leu Ser Leu Leu Tyr Lys Arg Leu Ile Gly Pro Lys Val Leu
            445                 450                 455 gct gtg cat gtg gct ggg ctc cag cgg aag cca cgg cct ggc cga gtg    1444
Ala Val His Val Ala Gly Leu Gln Arg Lys Pro Arg Pro Gly Arg Val
        460                 465                 470 atc cgg gac aaa cta agg att tat gct cac tgc aca aac cac cac aac    1492
Ile Arg Asp Lys Leu Arg Ile Tyr Ala His Cys Thr Asn His His Asn
    475                 480                 485 cac aac tac gtt cgt ggg tcc att aca ctt ttt atc atc aac ttg cat    1540
His Asn Tyr Val Arg Gly Ser Ile Thr Leu Phe Ile Ile Asn Leu His
490                 495                 500                 505 cga tca aga aag aaa atc aag ctg gct ggg act ctc aga gac aag ctg    1588
Arg Ser Arg Lys Lys Ile Lys Leu Ala Gly Thr Leu Arg Asp Lys Leu
                510                 515                 520 gtt cac cag tac ctg ctg cag ccc tat ggg cag gag ggc cta aag tcc    1636
Val His Gln Tyr Leu Leu Gln Pro Tyr Gly Gln Glu Gly Leu Lys Ser
            525                 530                 535 aag tca gtg caa ctg aat ggc cag ccc tta gtg atg gtg gac gac ggg    1684
Lys Ser Val Gln Leu Asn Gly Gln Pro Leu Val Met Val Asp Asp Gly
        540                 545                 550 acc ctc cca gaa ttg aag ccc cgc ccc ctt cgg gcc ggc cgg aca ttg    1732
Thr Leu Pro Glu Leu Lys Pro Arg Pro Leu Arg Ala Gly Arg Thr Leu
    555                 560                 565 gtc atc cct cca gtc acc atg ggc ttt ttt gtg gtc aag aat gtc aat    1780
Val Ile Pro Pro Val Thr Met Gly Phe Phe Val Val Lys Asn Val Asn
570                 575                 580                 585 gct ttg gcc tgc cgc tac cga taagctatcc tcacactcat ggctaccagt       1831
Ala Leu Ala Cys Arg Tyr Arg
                590 gggcctgctg gctgcttcc actcctccac tccagtagta tcctctgttt tcagacatcc   1891 tagcaaccag cccctgctgc cccatcctgc tggaatcaac acagacttgc tctccaaaga  1951 gactaaatgt catagcgtga tcttagccta ggtaggccac atccatccca aaggaaaatg  2011 tagacatcac ctgtacctat ataaggataa aggcatgtgt atagagcaa              2060

<210> SEQ ID NO 3
<211> LENGTH: 592
<212> TYPE: PRT
<213> ORGANISM: Homo sapiens

<400> SEQUENCE: 3

Met Arg Val Leu Cys Ala Phe Pro Glu Ala Met Pro Ser Ser Asn Ser
1               5                   10                  15

Arg Pro Pro Ala Cys Leu Ala Pro Gly Ala Leu Tyr Leu Ala Leu Leu
            20                  25                  30

Leu His Leu Ser Leu Ser Ser Gln Ala Gly Asp Arg Arg Pro Leu Pro
        35                  40                  45

Val Asp Arg Ala Ala Gly Leu Lys Glu Lys Thr Leu Ile Leu Leu Asp
    50                  55                  60

Val Ser Thr Lys Asn Pro Val Arg Thr Val Asn Glu Asn Phe Leu Ser
65                  70                  75                  80
```

-continued

```
Leu Gln Leu Asp Pro Ser Ile Ile His Asp Gly Trp Leu Asp Phe Leu
                85                  90                  95
Ser Ser Lys Arg Leu Val Thr Leu Ala Arg Gly Leu Ser Pro Ala Phe
            100                 105                 110
Leu Arg Phe Gly Gly Lys Arg Thr Asp Phe Leu Gln Phe Gln Asn Leu
        115                 120                 125
Arg Asn Pro Ala Lys Ser Arg Gly Gly Pro Gly Pro Asp Tyr Tyr Leu
    130                 135                 140
Lys Asn Tyr Glu Asp Asp Ile Val Arg Ser Asp Val Ala Leu Asp Lys
145                 150                 155                 160
Gln Lys Gly Cys Lys Ile Ala Gln His Pro Asp Val Met Leu Glu Leu
                165                 170                 175
Gln Arg Glu Lys Ala Ala Gln Met His Leu Val Leu Leu Lys Glu Gln
            180                 185                 190
Phe Ser Asn Thr Tyr Ser Asn Leu Ile Leu Thr Ala Arg Ser Leu Asp
        195                 200                 205
Lys Leu Tyr Asn Phe Ala Asp Cys Ser Gly Leu His Leu Ile Phe Ala
    210                 215                 220
Leu Asn Ala Leu Arg Arg Asn Pro Asn Asn Ser Trp Asn Ser Ser Ser
225                 230                 235                 240
Ala Leu Ser Leu Leu Lys Tyr Ser Ala Ser Lys Lys Tyr Asn Ile Ser
                245                 250                 255
Trp Glu Leu Gly Asn Glu Pro Asn Asn Tyr Arg Thr Met His Gly Arg
            260                 265                 270
Ala Val Asn Gly Ser Gln Leu Gly Lys Asp Tyr Ile Gln Leu Lys Ser
        275                 280                 285
Leu Leu Gln Pro Ile Arg Ile Tyr Ser Arg Ala Ser Leu Tyr Gly Pro
    290                 295                 300
Asn Ile Gly Arg Pro Arg Lys Asn Val Ile Ala Leu Leu Asp Gly Phe
305                 310                 315                 320
Met Lys Val Ala Gly Ser Thr Val Asp Ala Val Thr Trp Gln His Cys
                325                 330                 335
Tyr Ile Asp Gly Arg Val Val Lys Val Met Asp Phe Leu Lys Thr Arg
            340                 345                 350
Leu Leu Asp Thr Leu Ser Asp Gln Ile Arg Lys Ile Gln Lys Val Val
        355                 360                 365
Asn Thr Tyr Thr Pro Gly Lys Lys Ile Trp Leu Glu Gly Val Val Thr
    370                 375                 380
Thr Ser Ala Gly Gly Thr Asn Asn Leu Ser Asp Ser Tyr Ala Ala Gly
385                 390                 395                 400
Phe Leu Trp Leu Asn Thr Leu Gly Met Leu Ala Asn Gln Gly Ile Asp
                405                 410                 415
Val Val Ile Arg His Ser Phe Phe Asp His Gly Tyr Asn His Leu Val
            420                 425                 430
Asp Gln Asn Phe Asn Pro Leu Pro Asp Tyr Trp Leu Ser Leu Leu Tyr
        435                 440                 445
Lys Arg Leu Ile Gly Pro Lys Val Leu Ala Val His Val Ala Gly Leu
    450                 455                 460
Gln Arg Lys Pro Arg Pro Gly Arg Val Ile Arg Asp Lys Leu Arg Ile
465                 470                 475                 480
Tyr Ala His Cys Thr Asn His His Asn His Asn Tyr Val Arg Gly Ser
                485                 490                 495
```

```
Ile Thr Leu Phe Ile Ile Asn Leu His Arg Ser Arg Lys Lys Ile Lys
                500                 505                 510
Leu Ala Gly Thr Leu Arg Asp Lys Leu Val His Gln Tyr Leu Leu Gln
            515                 520                 525
Pro Tyr Gly Gln Glu Gly Leu Lys Ser Lys Ser Val Gln Leu Asn Gly
        530                 535                 540
Gln Pro Leu Val Met Val Asp Asp Gly Thr Leu Pro Glu Leu Lys Pro
545                 550                 555                 560
Arg Pro Leu Arg Ala Gly Arg Thr Leu Val Ile Pro Pro Val Thr Met
                565                 570                 575
Gly Phe Phe Val Val Lys Asn Val Asn Ala Leu Ala Cys Arg Tyr Arg
                580                 585                 590
```

<210> SEQ ID NO 4
<211> LENGTH: 1898
<212> TYPE: DNA
<213> ORGANISM: Homo sapiens

<400> SEQUENCE: 4

| | | | | | |
|---|---|---|---|---|---|
| cgcttaattc | tagaagaggg | attgaatgag | ggtgctttgt | gccttccctg | aagccatgcc | 60 |
| ctccagcaac | tcccgccccc | ccgcgtgcct | agccccgggg | gctctctact | tggctctgtt | 120 |
| gctccatctc | tcccttttcct | cccaggctgg | agacaggaga | cccttgcctg | tagacagagc | 180 |
| tgcaggtttg | aaggaaaaga | ccctgattct | acttgatgtg | agcaccaaga | acccagtcag | 240 |
| gacagtcaat | gagaacttcc | tctctctgca | gctggatccg | tccatcattc | atgatggctg | 300 |
| gctcgatttc | ctaagctcca | agcgcttggt | gaccctggcc | cggggacttt | cgcccgcctt | 360 |
| tctgcgcttc | gggggcaaaa | ggaccgactt | cctgcagttc | cagaacctga | ggaacccggc | 420 |
| gaaaagccgc | gggggcccgg | gccggattac | tatctcaaa | aactatgagg | atgccaggtc | 480 |
| tctagacaaa | ctttataact | tgctgattg | ctctggactc | cacctgatat | ttgctctaaa | 540 |
| tgcactgcgt | cgtaatccca | ataactcctg | gaacagttct | agtgccctga | gtctgttgaa | 600 |
| gtacagcgcc | agcaaaaagt | acaacatttc | ttgggaactg | ggtaatgagc | caaataacta | 660 |
| tcggaccatg | catggccggg | cagtaaatgg | cagccagttg | ggaaaggatt | acatccagct | 720 |
| gaagagcctg | ttgcagccca | tccggattta | ttccagagcc | agcttatatg | ccctaatat | 780 |
| tgggcggccg | aggaagaatg | tcatcgccct | cctagatgga | ttcatgaagg | tggcaggaag | 840 |
| tacagtagat | gcagttacct | ggcaacattg | ctacattgat | ggccgggtgg | tcaaggtgat | 900 |
| ggacttcctg | aaaactcgcc | tgttagacac | actctctgac | cagattagga | aaattcagaa | 960 |
| agtggttaat | acatacactc | caggaaagaa | gatttggctt | gaaggtgtgg | tgaccacctc | 1020 |
| agctggaggc | acaaacaatc | tatccgattc | ctatgctgca | ggattcttat | ggttgaacac | 1080 |
| tttaggaatg | ctggccaatc | agggcattga | tgtcgtgata | cggcactcat | tttttgacca | 1140 |
| tggatacaat | cacctcgtgg | accagaattt | taacccatta | ccagactact | ggctctctct | 1200 |
| cctctacaag | cgcctgatcg | gccccaaagt | cttggctgtg | catgtggctg | gctccagcg | 1260 |
| gaagccacgg | cctggccgag | tgatccggga | caaactaagg | atttatgctc | actgcacaaa | 1320 |
| ccaccacaac | cacaactacg | ttcgtgggtc | cattacactt | tttatcatca | acttgcatcg | 1380 |
| atcaagaaag | aaaatcaagc | tggctgggac | tctcagagac | aagctggttc | accagtacct | 1440 |
| gctgcagccc | tatgggcagg | agggcctaaa | gtccaagtca | gtgcaactga | atggccagcc | 1500 |
| cttagtgatg | gtggacgacg | ggaccctccc | agaattgaag | ccccgccccc | ttcgggccgg | 1560 |
| ccggacattg | gtcatccctc | cagtcaccat | gggcttttt | gtggtcaaga | atgtcaatgc | 1620 |

```
tttggcctgc cgctaccgat aagctatcct cacactcatg gctaccagtg ggcctgctgg    1680
gctgcttcca ctcctccact ccagtagtat cctctgtttt cagacatcct agcaaccagc    1740
ccctgctgcc ccatcctgct ggaatcaaca cagacttgct ctccaaagag actaaatgtc    1800
atagcgtgat cttagcctag gtaggccaca tccatcccaa aggaaaatgt agacatcacc    1860
tgtacctata taaggataaa ggcatgtgta tagagcaa                            1898
```

<210> SEQ ID NO 5
<211> LENGTH: 538
<212> TYPE: PRT
<213> ORGANISM: Homo sapiens

<400> SEQUENCE: 5

```
Met Arg Val Leu Cys Ala Phe Pro Glu Ala Met Pro Ser Ser Asn Ser
1               5                   10                  15

Arg Pro Pro Ala Cys Leu Ala Pro Gly Ala Leu Tyr Leu Ala Leu Leu
            20                  25                  30

Leu His Leu Ser Leu Ser Ser Gln Ala Gly Asp Arg Arg Pro Leu Pro
        35                  40                  45

Val Asp Arg Ala Ala Gly Leu Lys Glu Lys Thr Leu Ile Leu Leu Asp
    50                  55                  60

Val Ser Thr Lys Asn Pro Val Arg Thr Val Asn Glu Asn Phe Leu Ser
65                  70                  75                  80

Leu Gln Leu Asp Pro Ser Ile Ile His Asp Gly Trp Leu Asp Phe Leu
                85                  90                  95

Ser Ser Lys Arg Leu Val Thr Leu Ala Arg Gly Leu Ser Pro Ala Phe
            100                 105                 110

Leu Arg Phe Gly Gly Lys Arg Thr Asp Phe Leu Gln Phe Gln Asn Leu
        115                 120                 125

Arg Asn Pro Ala Lys Ser Arg Gly Gly Pro Gly Pro Asp Tyr Tyr Leu
    130                 135                 140

Lys Asn Tyr Glu Asp Ala Arg Ser Leu Asp Lys Leu Tyr Asn Phe Ala
145                 150                 155                 160

Asp Cys Ser Gly Leu His Leu Ile Phe Ala Leu Asn Ala Leu Arg Arg
                165                 170                 175

Asn Pro Asn Asn Ser Trp Asn Ser Ser Ala Leu Ser Leu Leu Lys
            180                 185                 190

Tyr Ser Ala Ser Lys Lys Tyr Asn Ile Ser Trp Glu Leu Gly Asn Glu
        195                 200                 205

Pro Asn Asn Tyr Arg Thr Met His Gly Arg Ala Val Asn Gly Ser Gln
    210                 215                 220

Leu Gly Lys Asp Tyr Ile Gln Leu Lys Ser Leu Leu Gln Pro Ile Arg
225                 230                 235                 240

Ile Tyr Ser Arg Ala Ser Leu Tyr Gly Pro Asn Ile Gly Arg Pro Arg
                245                 250                 255

Lys Asn Val Ile Ala Leu Leu Asp Gly Phe Met Lys Val Ala Gly Ser
            260                 265                 270

Thr Val Asp Ala Val Thr Trp Gln His Cys Tyr Ile Asp Gly Arg Val
        275                 280                 285

Val Lys Val Met Asp Phe Leu Lys Thr Arg Leu Leu Asp Thr Leu Ser
    290                 295                 300

Ala Gln Ile Arg Lys Ile Gln Lys Val Val Asn Thr Tyr Thr Pro Gly
305                 310                 315                 320
```

```
Lys Lys Ile Trp Leu Glu Gly Val Val Thr Thr Ser Ala Gly Gly Thr
                325                 330                 335

Asn Asn Leu Ser Asp Ser Tyr Ala Ala Gly Phe Leu Trp Leu Asn Thr
            340                 345                 350

Leu Gly Met Leu Ala Asn Gln Gly Ile Asp Val Val Ile Arg His Ser
        355                 360                 365

Phe Phe Asp His Gly Tyr Asn His Leu Val Asp Gln Asn Phe Asn Pro
    370                 375                 380

Leu Pro Asp Tyr Trp Leu Ser Leu Leu Tyr Lys Arg Leu Ile Gly Pro
385                 390                 395                 400

Lys Val Leu Ala Val His Val Ala Gly Leu Gln Arg Lys Pro Arg Pro
                405                 410                 415

Gly Arg Val Ile Arg Asp Lys Leu Arg Ile Tyr Ala His Cys Thr Asn
            420                 425                 430

His His Asn His Asn Tyr Val Arg Gly Ser Ile Thr Leu Phe Ile Ile
        435                 440                 445

Asn Leu His Arg Ser Arg Lys Lys Ile Lys Leu Ala Gly Thr Leu Arg
    450                 455                 460

Asp Lys Leu Val His Gln Tyr Leu Leu Gln Pro Tyr Gly Gln Glu Gly
465                 470                 475                 480

Leu Lys Ser Lys Ser Val Gln Leu Asn Gly Gln Pro Leu Val Met Val
                485                 490                 495

Asp Asp Gly Thr Leu Pro Glu Leu Lys Pro Arg Pro Leu Arg Ala Gly
            500                 505                 510

Arg Thr Leu Val Ile Pro Pro Val Thr Met Gly Phe Val Val Lys
        515                 520                 525

Asn Val Asn Ala Leu Ala Cys Arg Tyr Arg
    530                 535

<210> SEQ ID NO 6
<211> LENGTH: 1724
<212> TYPE: DNA
<213> ORGANISM: Homo sapiens

<400> SEQUENCE: 6
cgcttaattc tagaagaggg attgaatgag ggtgctttgt gccttccctg aagccatgcc      60
ctccagcaac tcccgccccc ccgcgtgcct agccccgggg gctctctact tggctctgtt     120
gctccatctc tccctttcct cccaggctgg agacaggaga cccttgcctg tagacagagc     180
tgcaggtttg aaggaaaaga ccctgattct acttgatgtg agcaccaaga acccagtcag     240
gacagtcaat gagaacttcc tctctctgca gctggatccg tccatcattc atgatggctg     300
gctcgatttc ctaagctcca agcgcttggt gaccctggcc cggggacttt cgcccgcctt     360
tctgcgcttc gggggcaaaa ggaccgactt cctgcagttc agaacctga ggaacccggc      420 gaaaagccgc gggggcccgg gcccggatta ctatctcaaa aactatgagg atgagccaaa     480
taactatcgg accatgcatg ccgggcagt aaatggcagc cagttgggaa aggattacat      540
ccagctgaag agcctgttgc agcccatccg gatttattcc agagccagct atatggccc      600 taatattggg cggccgagga agaatgtcat cgccctccta gatggattca tgaaggtggc     660
aggaagtaca gtagatgcag ttacctggca acattgctac attgatggcc gggtggtcaa     720
ggtgatggac ttcctgaaaa ctcgcctgtt agacacactc tctgaccaga ttaggaaaat     780
tcagaaagtg gttaatacat acactccagg aaagaagatt tggcttgaag tgtggtgac      840 caccctcagct ggaggcacaa acaatctatc cgattcctat gctgcaggat tcttatggtt     900
```

```
gaacacttta ggaatgctgg ccaatcaggg cattgatgtc gtgatacggc actcattttt    960
tgaccatgga tacaatcacc tcgtggacca gaattttaac ccattaccag actactggct   1020
ctctctcctc tacaagcgcc tgatcggccc caaagtcttg gctgtgcatg tggctgggct   1080
ccagcggaag ccacggcctg ccgagtgat ccgggacaaa ctaaggattt atgctcactg    1140
cacaaaccac cacaaccaca actacgttcg tgggtccatt acactttta tcatcaactt    1200 gcatcgatca agaaagaaaa tcaagctggc tgggactctc agagacaagc tggttcacca   1260
gtacctgctg cagccctatg ggcaggaggg cctaaagtcc aagtcagtgc aactgaatgg   1320 ccagcccta gtgatggtgg acgacgggac cctcccagaa ttgaagcccc gccccttcg    1380 ggccggccgg acattggtca tccctccagt caccatgggc tttttgtgg tcaagaatgt   1440 caatgctttg gcctgccgct accgataagc tatcctcaca ctcatggcta ccagtgggcc   1500
tgctgggctg cttccactcc tccactccag tagtatcctc tgttttcaga catcctagca   1560
accagcccct gctgccccat cctgctggaa tcaacacaga cttgctctcc aaagagacta   1620
aatgtcatag cgtgatctta gcctaggtag gccacatcca tcccaaagga aaatgtagac   1680
atcacctgta cctatataag gataaaggca tgtgtataga gcaa                    1724
```

<210> SEQ ID NO 7
<211> LENGTH: 480
<212> TYPE: PRT
<213> ORGANISM: Homo sapiens

<400> SEQUENCE: 7

```
Met Arg Val Leu Cys Ala Phe Pro Glu Ala Met Pro Ser Ser Asn Ser
1               5                  10                  15

Arg Pro Pro Ala Cys Leu Ala Pro Gly Ala Leu Tyr Leu Ala Leu Leu
            20                  25                  30

Leu His Leu Ser Leu Ser Ser Gln Ala Gly Asp Arg Arg Pro Leu Pro
        35                  40                  45

Val Asp Arg Ala Ala Gly Leu Lys Glu Lys Thr Leu Ile Leu Leu Asp
    50                  55                  60

Val Ser Thr Lys Asn Pro Val Arg Thr Val Asn Glu Asn Phe Leu Ser
65                  70                  75                  80

Leu Gln Leu Asp Pro Ser Ile Ile His Asp Gly Trp Leu Asp Phe Leu
                85                  90                  95

Ser Ser Lys Arg Leu Val Thr Leu Ala Arg Gly Leu Ser Pro Ala Phe
            100                 105                 110

Leu Arg Phe Gly Gly Lys Arg Thr Asp Phe Leu Gln Phe Gln Asn Leu
        115                 120                 125

Arg Asn Pro Ala Lys Ser Arg Gly Gly Pro Gly Pro Asp Tyr Tyr Leu
    130                 135                 140

Lys Asn Tyr Glu Asp Glu Pro Asn Asn Tyr Arg Thr Met His Gly Arg
145                 150                 155                 160

Ala Val Asn Gly Ser Gln Leu Gly Lys Asp Tyr Ile Gln Leu Lys Ser
                165                 170                 175

Leu Leu Gln Pro Ile Arg Ile Tyr Ser Arg Ala Ser Leu Tyr Gly Pro
            180                 185                 190

Asn Ile Gly Arg Pro Arg Lys Asn Val Ile Ala Leu Leu Asp Gly Phe
        195                 200                 205

Met Lys Val Ala Gly Ser Thr Val Asp Ala Val Thr Trp Gln His Cys
    210                 215                 220
```

Tyr Ile Asp Gly Arg Val Val Lys Val Met Asp Phe Leu Lys Thr Arg
225                 230                 235                 240

Leu Leu Asp Thr Leu Ser Asp Gln Ile Arg Lys Ile Gln Lys Val Val
                245                 250                 255

Asn Thr Tyr Thr Pro Gly Lys Lys Ile Trp Leu Glu Gly Val Val Thr
            260                 265                 270

Thr Ser Ala Gly Gly Thr Asn Asn Leu Ser Asp Ser Tyr Ala Ala Gly
        275                 280                 285

Phe Leu Trp Leu Asn Thr Leu Gly Met Leu Ala Asn Gln Gly Ile Asp
290                 295                 300

Val Val Ile Arg His Ser Phe Phe Asp His Gly Tyr Asn His Leu Val
305                 310                 315                 320

Asp Gln Asn Phe Asn Pro Leu Pro Asp Tyr Trp Leu Ser Leu Leu Tyr
                325                 330                 335

Lys Arg Leu Ile Gly Pro Lys Val Leu Ala Val His Val Ala Gly Leu
            340                 345                 350

Gln Arg Lys Pro Arg Pro Gly Arg Val Ile Arg Asp Lys Leu Arg Ile
        355                 360                 365

Tyr Ala His Cys Thr Asn His His Asn His Asn Tyr Val Arg Gly Ser
370                 375                 380

Ile Thr Leu Phe Ile Ile Asn Leu His Arg Ser Arg Lys Lys Ile Lys
385                 390                 395                 400

Leu Ala Gly Thr Leu Arg Asp Lys Leu Val His Gln Tyr Leu Leu Gln
                405                 410                 415

Pro Tyr Gly Gln Glu Gly Leu Lys Ser Lys Ser Val Gln Leu Asn Gly
            420                 425                 430

Gln Pro Leu Val Met Val Asp Asp Gly Thr Leu Pro Glu Leu Lys Pro
        435                 440                 445

Arg Pro Leu Arg Ala Gly Arg Thr Leu Val Ile Pro Pro Val Thr Met
450                 455                 460

Gly Phe Phe Val Val Lys Asn Val Asn Ala Leu Ala Cys Arg Tyr Arg
465                 470                 475                 480

<210> SEQ ID NO 8
<211> LENGTH: 351
<212> TYPE: DNA
<213> ORGANISM: Mus musculus

<400> SEQUENCE: 8
gttcggcaga ggatcatgtc tgatgtacag agacattgtc cggagtgatg ttgccttgga      60
caagcagaaa ggctgtaaga ttggccagca ccctgatgtc atgctggagc tccagagaga    120
gaaggcatcc agactgtctg gttcttctga aggagcaata ctccaatact acagtaacc     180 tcatattaac aggtctctag acaaacttta taactttgct gattgctctg gactccacct    240
gatatttgct ctaaatgcac tgcgtcgtaa tcccaataac tcctggaaca gttctagtgc    300
cctgagcctg ttgaagtaca gtgccagcaa aaagtacaac atttcttggg a             351

<210> SEQ ID NO 9
<211> LENGTH: 543
<212> TYPE: PRT
<213> ORGANISM: Homo sapiens

<400> SEQUENCE: 9

Met Leu Leu Arg Ser Lys Pro Ala Leu Pro Pro Pro Leu Met Leu Leu
1               5                   10                  15

Leu Leu Gly Pro Leu Gly Pro Leu Ser Pro Gly Ala Leu Pro Arg Pro
            20                  25                  30

Ala Gln Ala Gln Asp Val Val Asp Leu Asp Phe Phe Thr Gln Glu Pro
            35                  40                  45

Leu His Leu Val Ser Pro Ser Phe Leu Ser Val Thr Ile Asp Ala Asn
    50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
                100                 105                 110

Glu Glu Arg Ser Tyr Trp Gln Ser Gln Val Asn Gln Asp Ile Cys Lys
            115                 120                 125

Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
                180                 185                 190

Arg Thr Ala Asp Leu Gln Trp Asn Ser Ser Asn Ala Gln Leu Leu Leu
            195                 200                 205

Asp Tyr Cys Ser Ser Lys Gly Tyr Asn Ile Ser Trp Glu Leu Gly Asn
    210                 215                 220

Glu Pro Asn Ser Phe Leu Lys Lys Ala Asp Ile Phe Ile Asn Gly Ser
225                 230                 235                 240

Gln Leu Gly Glu Asp Tyr Ile Gln Leu His Lys Leu Leu Arg Lys Ser
                245                 250                 255

Thr Phe Lys Asn Ala Lys Leu Tyr Gly Pro Asp Val Gly Gln Pro Arg
                260                 265                 270

Arg Lys Thr Ala Lys Met Leu Lys Ser Phe Leu Lys Ala Gly Gly Glu
            275                 280                 285

Val Ile Asp Ser Val Thr Trp His His Tyr Tyr Leu Asn Gly Arg Thr
    290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
    355                 360                 365

Leu Gly Leu Ser Ala Arg Met Gly Ile Glu Val Val Met Arg Gln Val
    370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
                420                 425                 430

Val Tyr Leu His Cys Thr Asn Thr Asp Asn Pro Arg Tyr Lys Glu Gly

```
                435                 440                 445
Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
    530                 535                 540

<210> SEQ ID NO 10
<211> LENGTH: 23
<212> TYPE: DNA
<213> ORGANISM: Synthetic Oligonucleotide

<400> SEQUENCE: 10
ggagagcaag tctgtgttga ttc                                              23

<210> SEQ ID NO 11
<211> LENGTH: 22
<212> TYPE: DNA
<213> ORGANISM: Synthetic Oligonucleotide

<400> SEQUENCE: 11
cactggtagc catgagtgtg ag                                               22

<210> SEQ ID NO 12
<211> LENGTH: 22
<212> TYPE: DNA
<213> ORGANISM: Synthetic Oligonucleotide

<400> SEQUENCE: 12
ttggtcatcc ctccagtcac ca                                               22

<210> SEQ ID NO 13
<211> LENGTH: 2
<212> TYPE: PRT
<213> ORGANISM: Homo sapiens

<400> SEQUENCE: 13

Asp Glu
1

<210> SEQ ID NO 14
<211> LENGTH: 23
<212> TYPE: DNA
<213> ORGANISM: Synthetic Oligonucleotide

<400> SEQUENCE: 14
cttgcctgta gacagagctg cag                                              23

<210> SEQ ID NO 15
<211> LENGTH: 2396
<212> TYPE: DNA
<213> ORGANISM: Mus musculus

<400> SEQUENCE: 15
```

-continued

```
tttctagttg cttttagcca atgtcggatc aggtttttca agcgacaaag agatactgag      60
atcctgggca gaggacatcc tagctcggtc agatttgggc aggctcaagt gaccagtgtc     120
ttaaggcaga agggagtcgg ggtagggtct ggctgaaccc tcaaccgggg cttttaactc     180
agggtctagt cctggcgcca aatggatggg acctagaaaa ggtgacagag tgcgcaggac     240
accaggaagc tggtcccacc cctgcgcggc tcccggcgcg tccctcccca ggcctccgag     300
gatcttggat tctggccacc tccgcaccct ttggatgggt gtggatgatt tcaaaagtgg     360
acgtgaccgc ggcggagggg aaagccagca cggaaatgaa agagagcgag gaggggaggg     420
cggggagggg agggcgctag ggagggactc ccggagggg tgggagggat ggagcgctgt      480
gggagggtac tgagtcctgg cgccagaggc gaagcaggac cggttgcagg gggcttgagc     540
cagcgcgccg gctgccccag ctctcccggc agcgggcggt ccagccaggt gggatgctga     600
ggctgctgct gctgtggctc tggggccgc tcggtgccct ggcccagggc gccccgcgg      660 ggaccgcgcc gaccgacgac gtggtagact tggagtttta caccaagcgg ccgctccgaa     720
gcgtgagtcc ctcgttcctg tccatcacca tcgacgccag cctggccacc gacccgcgct     780
tcctcacctt cctgggctct ccaaggctcc gtgctctggc tagaggctta tctcctgcat     840
acttgagatt tggcggcaca aagactgact tccttatttt tgatccggac aaggaaccga     900
cttccgaaga aagaagttac tggaaatctc aagtcaacca tgatatttgc aggtctgagc     960
cggtctctgc tgcggtgttg aggaaactcc aggtggaatg gcccttccag gagctgttgc    1020
tgctccgaga gcagtaccaa aaggagttca gaacagcac ctactcaaga agctcagtgg     1080
acatgctcta cagttttgcc aagtgctcgg ggttagacct gatctttggt ctaaatgcgt    1140
tactacgaac cccagactta cggtggaaca gctccaacgc ccagcttctc cttgactact    1200
gctcttccaa gggttataac atctcctggg aactgggcaa tgagcccaac agtttctgga    1260
agaaagctca cattctcatc gatgggttgc agttaggaga agactttgtg gagttgcata    1320
aacttctaca aaggtcagct ttccaaaatg caaaactcta tggtcctgac atcggtcagc    1380
ctcgagggaa gacagttaaa ctgctgagga gtttcctgaa ggctggcgga gaagtgatcg    1440
actctcttac atggcatcac tattacttga atggacgcat cgctaccaaa gaagatttttc   1500 tgagctctga tgcgctggac acttttattc tctctgtgca aaaaattctg aaggtcacta    1560
aagagatcac acctggcaag aaggtctggt tgggagagac gagctcagct tacggtggcg    1620 gtgcacccctt gctgtccaac accttttgcag ctggctttat gtggctggat aaattgggcc   1680
tgtcagccca gatgggcata gaagtcgtga tgaggcaggt gttcttcgga gcaggcaact    1740 accactagt ggatgaaaac tttgagcctt tacctgatta ctggctctct cttctgttca      1800
agaaactggt aggtcccagg gtgttactgt caagagtgaa aggcccagac aggagcaaac    1860
tccgagtgta tctccactgc actaacgtct atcacccacg atatcaggaa ggagatctaa    1920
ctctgtatgt cctgaacctc cataatgtca ccaagcactt gaaggtaccg cctccgttgt    1980
tcaggaaacc agtggatacg taccttctga agccttcggg gccggatgga ttactttcca    2040
aatctgtcca actgaacggt caaattctga agatggtgga tgagcagacc ctgccagctt    2100
tgacagaaaa acctctcccc gcaggaagtg cactaagcct gcctgccttt tcctatggtt    2160
tttttgtcat aagaaatgcc aaaatcgctg cttgtatatg aaaataaaag gcatacggta    2220
cccctgagac aaaagccgag gggggtgtta ttcataaaac aaaaccctag tttaggaggc    2280
cacctccttg ccgagttcca gagcttcggg agggtgggt acacttcagt attacattca     2340
gtgtggtgtt ctctctaaga agaatactgc aggtggtgac agttaatagc actgtg        2396
```

```
<210> SEQ ID NO 16
<211> LENGTH: 22
<212> TYPE: DNA
<213> ORGANISM: Synthetic Oligonucleotide

<400> SEQUENCE: 16
gagcagccag gtgagcccaa ga                                          22

<210> SEQ ID NO 17
<211> LENGTH: 24
<212> TYPE: DNA
<213> ORGANISM: Synthetic Oligonucleotide

<400> SEQUENCE: 17
tcagatgcaa gcagcaactt tggc                                        24

<210> SEQ ID NO 18
<211> LENGTH: 21
<212> TYPE: DNA
<213> ORGANISM: Synthetic Oligonucleotide

<400> SEQUENCE: 18
caccctgatg tcatgctgga g                                           21

<210> SEQ ID NO 19
<211> LENGTH: 23
<212> TYPE: DNA
<213> ORGANISM: Synthetic Oligonucleotide

<400> SEQUENCE: 19
catctaggag agcaatgacg ttc                                         23

<210> SEQ ID NO 20
<211> LENGTH: 27
<212> TYPE: DNA
<213> ORGANISM: Synthetic Oligonucleotide

<400> SEQUENCE: 20
ccatcctaat acgactcact atagggc                                     27

<210> SEQ ID NO 21
<211> LENGTH: 23
<212> TYPE: DNA
<213> ORGANISM: Synthetic Oligonucleotide

<400> SEQUENCE: 21
actcactata gggctcgagc ggc                                         23

<210> SEQ ID NO 22
<211> LENGTH: 15
<212> TYPE: DNA
<213> ORGANISM: Synthetic Oligonucleotide

<400> SEQUENCE: 22
tttttttttt ttttt                                                  15

<210> SEQ ID NO 23
<211> LENGTH: 560
<212> TYPE: DNA
<213> ORGANISM: Homo sapiens

<400> SEQUENCE: 23
```

```
ggcacgaggc tagtggagag actgacaagc agtcagctca gcggtcacaa tactgtgtga    60
caggagctga gatccaagaa gtactgggtc ctgtgggagc ccccctgact tgaaggacaa   120
gtcagtgcaa ctgaatggcc agcccttagt gatggtggac gacgggaccc tcccagaatt   180
gaagccccgc cccttcgggc cggccggac attggtcatc cctccagtca ccatgggctt   240
ttttgtggtc aagaatgtca atgctttggc ctgccgctac cgataagcta tcctcacact   300
catggctacc agtgggcctg ctgggctgct tccactcctc cactccagta gtatcctctg   360
ttttcagaca tcctagcaac cagccccctgc tgccccatcc tgctggaatc aacacagact   420
tgctctccaa agagactaaa tgtcatagcg tgatcttagc ctaggtaggc cacatccatc   480
ccaaaggaaa atgtagacat cacctgtacc tatataagga taaaggcatg tgtatagagc   540
aaaaaaaaaa aaaaaaaaa                                               560

<210> SEQ ID NO 24
<211> LENGTH: 1721
<212> TYPE: DNA
<213> ORGANISM: Homo sapiens

<400> SEQUENCE: 24
ctagagcttt cgactctccg ctgcgcggca gctggcgggg ggagcagcca ggtgagccca    60
agatgctgct gcgctcgaag cctgcgctgc cgccgccgct gatgctgctg ctcctggggc   120
cgctgggtcc cctctcccct ggcgccctgc cccgacctgc gcaagcacag gacgtcgtgg   180
acctggactt cttcacccag gagccgctgc acctggtgag cccctcgttc ctgtccgtca   240
ccattgacgc caacctggcc acggacccgc ggttcctcat cctcctgggt tctccaaagc   300
ttcgtacctt ggccagaggc ttgtctcctg cgtacctgag gtttggtggc accaagacag   360
acttcctaat tttcgatccc aagaaggaat caaccttttga agagagaagt tactggcaat   420
ctcaagtcaa ccaggatatt tgcaaatatg gatccatccc tcctgatgtg gaggagaagt   480
tacggttgga atggccctac caggagcaat tgctactccg agaacactac cagaaaaagt   540
tcaagaacag cacctactca agaagctctg tagatgtgct atacactttt gcaaactgct   600
caggactgga cttgatcttt ggcctaaatg cgttattaag aacagcagat ttgcagtgga   660
acagttctaa tgctcagttg ctcctggact actgctcttc caaggggtat aacatttctt   720
gggaactagg caatgaacct aacagtttcc ttaagaaggc tgatattttc atcaatgggt   780
cgcagttagg agaagattat attcaattgc ataaacttct aagaaagtcc accttcaaaa   840
atgcaaaact ctatggtcct gatgttggtc agcctcgaag aaagacggct aagatgctga   900
agagcttcct gaaggctggt ggagaagtga ttgattcagt tacatggcat cactactatt   960
tgaatggacg gactgctacc agggaagatt ttctaaaccc tgatgtattg gacatttta   1020 tttcatctgt gcaaaaagtt tccaggtgg ttgagagcac caggcctggc aagaaggtct   1080
ggttaggaga aacaagctct gcatatggag gcggagcgcc cttgctatcc gacacctttg   1140
cagctggctt tatgtggctg ataaattgg gcctgtcagc ccgaatggga atagaagtgg   1200
tgatgaggca agtattcttt ggagcaggaa actaccattt agtggatgaa acttcgatc   1260 ctttacctga ttattggcta tctcttctgt tcaagaaatt ggtgggcacc aaggtgttaa   1320
tggcaagcgt gcaaggttca aagagaagga agcttcgagt ataccttcat gcacaaaca   1380 ctgacaatcc aagtgtataaa gaaggagatt taactctgta tgccataaac ctccataacg   1440
tcaccaagta cttgcggtta ccctatcctt tttctaacaa gcaagtggat aaataccttc   1500
taagaccttt gggacctcat ggattacttt ccaaatctgt ccaactcaat ggtctaactc   1560
```

```
taaagatggt ggatgatcaa accttgccac ctttaatgga aaaacctctc cggccaggaa    1620
gttcactggg cttgccagct ttctcatata gttttttgt gataagaaat gccaaagttg    1680
ctgcttgcat ctgaaaataa aatatactag tcctgacact g                        1721

<210> SEQ ID NO 25
<211> LENGTH: 45
<212> TYPE: DNA
<213> ORGANISM: Synthetic Oligonucleotide

<400> SEQUENCE: 25
cttacttgtc atcgtcgtcc ttgtagtctc ggtagcggca ggcca                    45
```